United States Patent
Ikeuchi et al.

(10) Patent No.: US 7,872,076 B2
(45) Date of Patent: Jan. 18, 2011

(54) PARTICULATE WATER-ABSORBENT RESIN COMPOSITION AND ITS PRODUCTION PROCESS

(75) Inventors: Hiroyuki Ikeuchi, Himeji (JP); Kazushi Torii, Himeji (JP); Taku Iwamura, Himeji (JP); Sayaka Machida, Himeji (JP); Hiroko Okochi, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 917 days.

(21) Appl. No.: 10/577,355

(22) PCT Filed: Nov. 5, 2004

(86) PCT No.: PCT/JP2004/016777
§ 371 (c)(1),
(2), (4) Date: Apr. 28, 2006

(87) PCT Pub. No.: WO2005/044915
PCT Pub. Date: May 19, 2005

(65) Prior Publication Data
US 2008/0139693 A1    Jun. 12, 2008

(30) Foreign Application Priority Data
Nov. 7, 2003  (JP) .............................. 2003-377898

(51) Int. Cl.
*C08F 120/06* (2006.01)
*C08K 5/053* (2006.01)

(52) U.S. Cl. .................................... 525/329.7; 523/111
(58) Field of Classification Search .................. 523/111; 525/329.7
See application file for complete search history.

(56) References Cited

U.S. PATENT DOCUMENTS

| | | | |
|---|---|---|---|
| 4,093,776 A | 6/1978 | Aoki et al. |
| 4,286,082 A | 8/1981 | Tsubakimoto et al. |
| 4,367,323 A | 1/1983 | Kitamura et al. |
| 4,446,261 A | 5/1984 | Yamasaki et al. |
| 4,625,001 A | 11/1986 | Tsubakimoto et al. |
| 4,666,983 A | 5/1987 | Tsubakimoto et al. |
| 4,683,274 A | 7/1987 | Nakamura et al. |
| 4,873,299 A | 10/1989 | Nowakowsky et al. |
| 4,973,632 A | 11/1990 | Nagasuna et al. |

(Continued)

FOREIGN PATENT DOCUMENTS

CN        1342174        3/2002

(Continued)

*Primary Examiner*—Satya B Sastri
(74) *Attorney, Agent, or Firm*—Roylance, Abrams, Berdo & Goodman, L.L.P.

(57) ABSTRACT

An object of the present invention is to provide a particulate water-absorbent resin composition and its production process, wherein the particulate water-absorbent resin composition is an enhanced one in both of the "liquid permeability" and "liquid-sucking-up property" (which have hitherto been antithetical physical properties) of the water-absorbent resin. As a means of achieving this object, a first particulate water-absorbent resin composition according to the present invention is a particulate water-absorbent resin composition comprising a water-absorbent resin (A) of a crosslinked structure obtained by polymerizing an acid-group-containing unsaturated monomer, with the composition being characterized by: having a particle size such that particles in the range of 850 to 150 μm (but not including 850 μm) account for not less than 90 weight % of the entirety; and containing a tetra- or more functional polyol (B) at least on surfaces.

21 Claims, 3 Drawing Sheets

U.S. PATENT DOCUMENTS

| | | |
|---|---|---|
| 4,985,518 A | 1/1991 | Alexander et al. |
| 5,026,800 A | 6/1991 | Kimura et al. |
| 5,051,259 A | 9/1991 | Olsen et al. |
| 5,124,416 A | 6/1992 | Haruna et al. |
| 5,145,906 A | 9/1992 | Chambers et al. |
| 5,164,459 A | 11/1992 | Kimura et al. |
| 5,244,735 A | 9/1993 | Kimura et al. |
| 5,250,640 A | 10/1993 | Irie et al. |
| 5,264,495 A | 11/1993 | Irie et al. |
| 5,380,808 A | 1/1995 | Sumiya et al. |
| 5,385,983 A | 1/1995 | Graham |
| 5,409,771 A | 4/1995 | Dahmen et al. |
| 5,447,727 A | 9/1995 | Graham |
| 5,797,893 A | 8/1998 | Wada et al. |
| 6,071,976 A | 6/2000 | Dairoku et al. |
| 6,087,002 A | 7/2000 | Kimura et al. |
| 6,127,454 A * | 10/2000 | Wada et al. ............... 523/200 |
| 6,228,930 B1 | 5/2001 | Dairoku et al. |
| 6,254,990 B1 | 7/2001 | Ishizaki et al. |
| 6,399,668 B1 | 6/2002 | Miyake et al. |
| 6,414,214 B1 | 7/2002 | Engelhardt et al. |
| 6,559,239 B1 | 5/2003 | Riegel et al. |
| 6,605,673 B1 * | 8/2003 | Mertens et al. ......... 525/329.5 |
| 6,911,572 B1 | 6/2005 | Bruhn et al. |
| 2002/0072471 A1 | 6/2002 | Ikeuchi et al. |
| 2002/0128618 A1 | 9/2002 | Frenz et al. |
| 2003/0020199 A1 | 1/2003 | Kajikawa et al. |
| 2003/0157318 A1 * | 8/2003 | Brehm et al. ............... 428/327 |
| 2004/0106745 A1 | 6/2004 | Nakashima et al. |
| 2004/0214946 A1 * | 10/2004 | Smith et al. ............... 524/556 |
| 2005/0245684 A1 | 11/2005 | Daniel et al. |

FOREIGN PATENT DOCUMENTS

| | | |
|---|---|---|
| EP | 0349240 | 1/1990 |
| EP | 0629411 | 12/1994 |
| EP | 0640330 | 3/1995 |
| EP | 0532002 | 5/1997 |
| EP | 0811636 | 12/1997 |
| EP | 0922717 | 6/1999 |
| EP | 0579764 | 8/1999 |
| EP | 0951913 | 10/1999 |
| EP | 0955086 | 11/1999 |
| JP | 58-183754 | 10/1983 |
| JP | 63-302834 | 12/1988 |
| JP | 4-214735 | 8/1992 |
| JP | 05-156034 | 6/1993 |
| JP | 8-506363 | 7/1996 |
| JP | 9-509591 | 9/1997 |
| JP | 9-309916 | 12/1997 |
| JP | 2000-342963 | 12/2000 |
| JP | 2002-138147 | 5/2002 |
| JP | 2002-539281 | 11/2002 |
| JP | 2003-062460 | 3/2003 |
| JP | 2003-82107 | 3/2003 |
| JP | 2003-105092 | 4/2003 |
| JP | 2000-539281 A * | 11/2008 |
| WO | WO 95/22356 | 8/1995 |
| WO | WO 95/26209 | 10/1995 |
| WO | WO 98/47454 | 10/1998 |
| WO | WO 99/64485 | 12/1999 |
| WO | WO 00/53644 | 9/2000 |
| WO | WO 01/66056 | 9/2001 |
| WO | WO 02/20068 | 3/2002 |
| WO | WO 2004/024816 | 3/2004 |

* cited by examiner

PARTICULATE WATER-ABSORBENT RESIN COMPOSITION AND ITS PRODUCTION PROCESS

TECHNICAL FIELD

The present invention relates to a particulate water-absorbent resin composition and its production process. More specifically, the present invention relates to a particulate water-absorbent resin composition and its production process, wherein the composition is low in the fine powder content and excellent in the liquid permeability and the liquid-sucking-up property.

BACKGROUND ART

In recent years, a water-absorbent resin is widely utilized in sanitary materials (absorbent articles) (e.g. disposable diapers, sanitary napkins, incontinent pads) and as their main component material in order to cause the water-absorbent resin to absorb body fluids (e.g. urine, blood).

Known examples of the above water-absorbent resin include: partially-neutralized and crosslinked poly(acrylic acids); hydrolyzed graft polymers of starch-acrylonitrile; neutralized graft polymers of starch-acrylic acid; saponified copolymers of vinyl acetate-acrylic acid esters; crosslinked carboxymethyl cellulose; hydrolyzed copolymers of acrylonitrile or acrylamide, or crosslinked polymers of these hydrolyzed copolymers; crosslinked polymers of cationic monomers; crosslinked copolymers of isobutylene-maleic acid; and crosslinked copolymers of 2-acrylamido-2-methyl-propanesulfonic acid and acrylic acid.

As water absorption properties which the above water-absorbent resin is desired to have, there have hitherto been preached such as, on occasions of contact with aqueous liquids (e.g. body fluids), high water absorption capacity, excellent absorption rate, liquid permeability, gel strength of swollen gel, suction amount of sucking up water from base materials containing the aqueous liquids.

In recent years, as to the sanitary materials (e.g. disposable diapers), their high functionalization and thinning are making progress. Thus, the thinning is aimed at while the increase of the absorption amount and the prevention of the leakage are aimed at by increasing the amount (g) and ratio (weight %/ratio in absorbent structure) of the water-absorbent resin being used. The sanitary materials in which the water-absorbent resin has been increased as mentioned above are on the favorable track from the viewpoint of simply storing a liquid. However, in practical use for diapers, the water-absorbent resin has had problems of, due to water absorption, swelling to thus form a soft gel, thereby causing what is called gel blocking in the diapers wherein the gel blocking causes the absorption amount reduction and the leakage.

Thus, the liquid permeability of the water-absorbent resin is taken notice of in recent years. For example, water-absorbent resins enhanced in the liquid permeability are reported (e.g. refer to patent documents 1 to 7 below). However, if attempts are made to cause prior water-absorbent resins to exercise high liquid permeability, then the enhancement of the liquid permeability needs the enlargement of particle diameters and the extension of spaces in the gel, so the water-absorbent resins which have high liquid permeability have generally had problems of deteriorating in the liquid-sticking-up property.

It has also been known that the particle size distribution contributes very much to the liquid permeability, and arts of controlling the particle size of the water-absorbent resin have also been known (e.g. refer to patent documents 8 to 11 below), but have had problems that the liquid-sucking-up property deteriorates if the particle size is enlarged. The liquid-sucking-up property is an important property having been known so far (e.g. refer to patent documents 12 and 13 below), but it has been very difficult to obtain a particulate water-absorbent resin composition enhanced in both of the "liquid permeability" and "liquid-sucking-up property" of the water-absorbent resin, because both are antithetical physical properties.

Incidentally, the "liquid permeability" in the present invention refers to the liquid permeation performance after the particulate water-absorbent resin composition has absorbed water under load, that is, liquid permeability between swollen gel particles under load, and is a liquid permeability model in diapers during practical use. In addition, the "liquid-sucking-up property" in the present invention refers to the liquid-sucking-up or liquid-distributing performance when a water-unabsorbed particulate water-absorbent resin composition absorbs water, that is, a rate at which water-unabsorbed dry particles suck up a liquid or a rate at which a liquid is distributed into the particulate water-absorbent resin composition, and is a liquid distribution model (which has not been found out until the present invention is made) in diapers during practical use.

[Patent Document 1] Pamphlet of WO 95/26209
[Patent Document 2] EP 0 951 913 B
[Patent Document 3] EP 0 640 330 B
[Patent Document 4] Pamphlet of WO 2001/066056
[Patent Document 5] Pamphlet of WO 98/47454
[Patent Document 6] U.S. Pat. No. 6,414,214
[Patent Document 7] US Patent Publication No. 2002/128618
[Patent Document 8] U.S. Pat. No. 5,051,259
[Patent Document 9] EP 0 349 240 B
[Patent Document 10] EP 0 579 764 B
[Patent Document 11] EP 0 629 411 B
[Patent Document 12] EP 0 532 002 B
[Patent Document 13] U.S. Pat. No. 6,399,668

DISCLOSURE OF THE INVENTION

Objects of the Invention

Accordingly, an object of the present invention is to provide a novel particulate water-absorbent resin composition and its production process, wherein the novel particulate water-absorbent resin composition is provided by providing a particulate water-absorbent resin composition enhanced in both of the "liquid permeability" and "liquid-sucking-up property" (which have hitherto been antithetical physical properties) of the water-absorbent resin and is used for disposable diapers and sanitary napkins. Another object of the present invention is to provide a particulate water-absorbent resin composition which is favorable for a high-concentration absorbent structure, that is, a particulate water-absorbent resin composition which is favorable for an absorbent structure that is high in concentration (weight ratio) of the particulate water-absorbent resin composition in an absorbent structure (another designation: core) of a disposable diaper or of a sanitary napkin.

SUMMARY OF THE INVENTION

The present inventors diligently studied to solve the above problems. As a result, the present inventors have found out that, (1) if the water-absorbent resin composition is a particulate water-absorbent resin composition controlled to a specific particle size and further, on its surfaces, there exists a tetra- or more functional polyol (B), or (2) if the water-absorbent resin composition is a particulate water-absorbent resin composition and, on its surfaces, there exist a tetra- or more functional polyol (B) and a tri- or more functional polycation, or (3) if the water-absorbent resin composition is a particulate water-absorbent resin composition controlled to a specific particle size and there is a specific relation between the liquid distribution velocity (LDV) of the composition and its water absorption capacity without load (CRC), or (4) if the water-absorbent resin composition is a particulate water-absorbent resin composition controlled to a specific particle size and the surface OH/C ratio as determined by photoelectron spectrometry is in a specific range, then this composition is a particulate water-absorbent resin composition which is excellent in the liquid permeability and the liquid-sucking-up property. In addition, the present inventors have further found out that such a particulate water-absorbent resin composition which is excellent in the liquid permeability and the liquid-sucking-up property can easily be produced if a water-absorbent resin controlled to a specific particle size is mixed with a tetra- or more functional polyol. The present invention has been completed in this way.

That is to say, a particulate water-absorbent resin composition according to the present invention is a particulate water-absorbent resin composition comprising a water-absorbent resin (A) of a crosslinked structure obtained by polymerizing an acid-group-containing unsaturated monomer, with the composition being characterized by: having a particle size such that particles in the range of 850 to 150 μm (but not including 850 μm) account for not less than 90 weight % of the entirety; and containing a tetra- or more functional polyol (B) at least on surfaces.

Another particulate water-absorbent resin composition according to the present invention is a particulate water-absorbent resin composition comprising a water-absorbent resin (A) of a crosslinked structure obtained by polymerizing an acid-group-containing unsaturated monomer, with the composition being characterized by containing a tetra- or more functional polyol (B) and a tri- or more functional polycation at least on surfaces.

Another particulate water-absorbent resin composition according to the present invention is a particulate water-absorbent resin composition comprising a water-absorbent resin (A) of a crosslinked structure obtained by polymerizing an acid-group-containing unsaturated monomer, with the composition being characterized by: having a particle size such that particles in the range of 850 to 150 μm (but not including 850 μm) account for not less than 90 weight % of the entirety; and satisfying the following relation: liquid distribution velocity (LDV) (mm/s)>−0.186×water absorption capacity without load (CRC) (g/g)+5.75 (wherein LDV>0.10 (mm/s)).

Another particulate water-absorbent resin composition according to the present invention is a particulate water-absorbent resin composition comprising a water-absorbent resin (A) of a crosslinked structure obtained by polymerizing an acid-group-containing unsaturated monomer, with the composition being characterized by: having a particle size such that particles in the range of 850 to 150 μm (but not including 850 μm) account for not less than 90 weight % of the entirety; and being in the range of 0.03 to 0.15 in surface OH/C ratio as determined by photoelectron spectrometry.

A process according to the present invention for production of a particulate water-absorbent resin composition is a process for production of a particulate water-absorbent resin composition including a water-absorbent resin (A) of a crosslinked structure obtained by polymerizing an acid-group-containing unsaturated monomer, with the process being characterized in that the water-absorbent resin (A) is such that particles in the range of 850 to 150 μm (but not including 850 μm) account for not less than 90 weight % of the entirety, and further in that the process includes a step of mixing the water-absorbent resin (A) and a tetra- or more functional polyol (B) together.

EFFECTS OF THE INVENTION

The present invention can provide a particulate water-absorbent resin composition and its production process, wherein the particulate water-absorbent resin composition is low in the fine powder content and is an enhanced one in both of the "liquid permeability" and "liquid-sucking-up property" (which have hitherto been antithetical physical properties) of the water-absorbent resin.

EXPLANATION OF THE SYMBOLS

Figure 1:
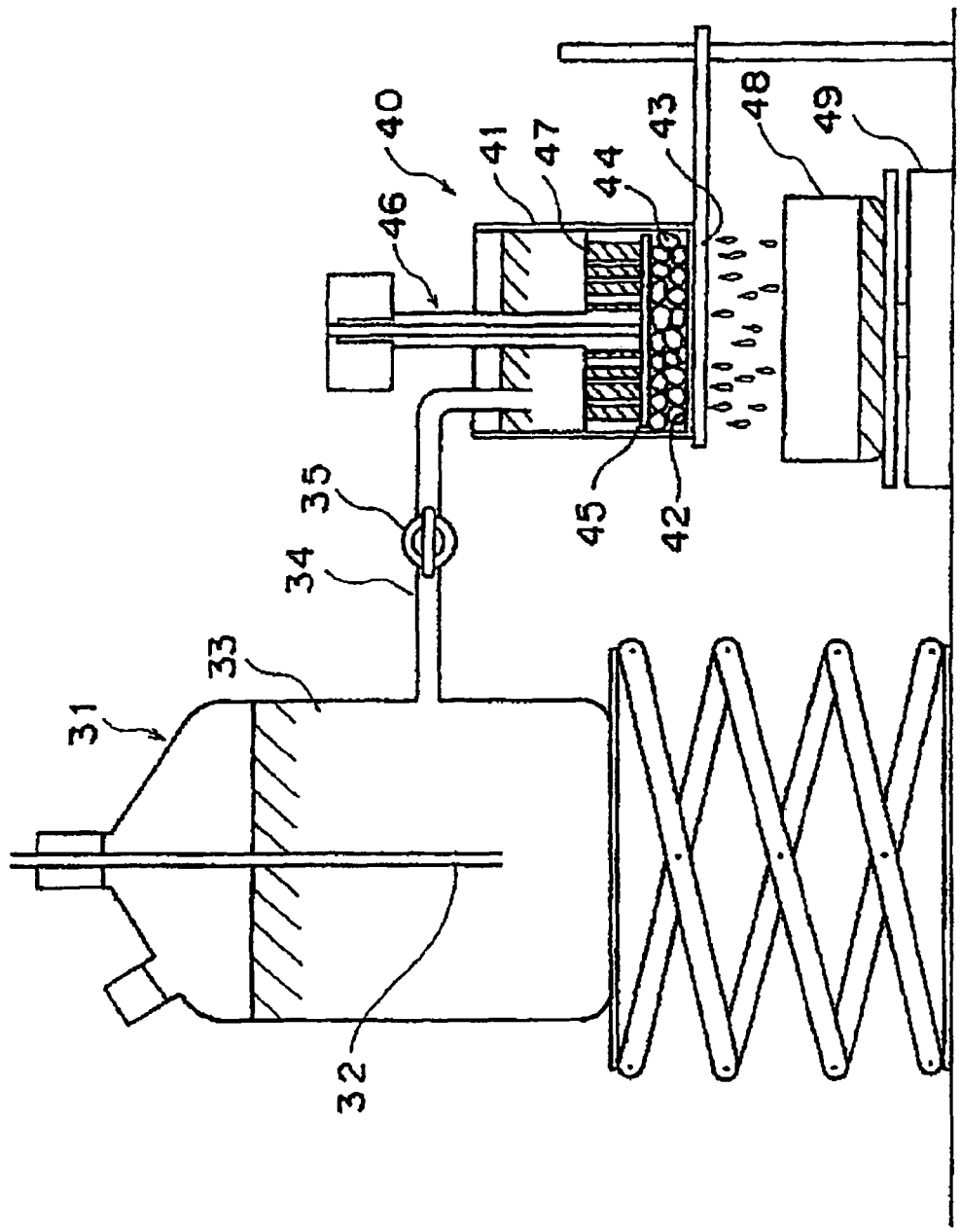
FIG. 1 is a schematic sectional view of a measurement apparatus as used for measuring the saline flow conductivity (SFC) of the water-absorbent resin composition.

31: Tank
32: Glass tube
33: 0.69 weight % aqueous sodium chloride solution
34: L-tube having cock
35: Cock
40: Receptacle
41: Cell
42: Stainless metal gauze
43: Stainless metal gauze
44: Swollen gel
45: Glass filter
46: Piston
47: Holes in piston
48: Collecting receptacle
49: Balance
51: Trough sheet
52: Trough groove
53: Screen
54: Crossbar
55: Experimental stand
56: Liquid reservoir tank
57: Liquid.
58: Experimental jack
59: Particulate water-absorbent resin composition (weight: 1 g, spread distance: 20 cm).

DETAILED DESCRIPTION OF THE INVENTION

Hereinafter, detailed descriptions are given about the present invention. However, the scope of the present invention is not bound to these descriptions. And other than the following illustrations can also be carried out in the form of appropriate modifications of the following illustrations within the scope not departing from the spirit of the present invention.

Incidentally, in the present invention, the "weight" is treated as a synonym of "mass", and the "weight %" is treated as a synonym of "mass %".

(1) Water-Absorbent Resin:

The water-absorbent resin in the present invention refers to a crosslinked polymer which is hydrogel-formable, water-swellable and water-insoluble. For example, the "water-swellable" refers to a water-absorbent resin which absorbs water in a large amount of essentially not less than 5 times, favorably 50 to 1,000 times, of its own weight in ion-exchanged water, and the "water-insoluble" refers to a water-absorbent resin in which the uncrosslinked water-extractable component (water-soluble polymer) content is favorably in the range of 0 to 50 weight %, more favorably not higher than 25 weight %, still more favorably not higher than 20 weight %, yet still more favorably not higher than 15 weight %, particularly favorably not higher than 10 weight %. Incidentally, the methods for measuring them are specified in the below-mentioned detailed description of Examples of some preferred embodiments.

In the present invention, the water-absorbent resin (A) of a crosslinked structure obtained by polymerizing an acid-group-containing unsaturated monomer is used as the water-absorbent resin favorably from the viewpoints of the liquid permeability and the liquid-sucking-up property.

Incidentally, as to the acid-group-containing unsaturated monomer, a monomer which will form the acid group by hydrolysis after the polymerization (e.g. acrylonitrile) is also taken as the acid-group-containing unsaturated monomer in the present invention. However, favorably, an acid-group-containing unsaturated monomer which contains the acid group during the polymerization is used.

Examples of the water-absorbent resin in the present invention include one or more of such as: partially-neutralized polymers of poly(acrylic acids); hydrolyzed graft polymers of starch-acrylonitrile; graft polymers of starch-acrylic acid; saponified copolymers of vinyl acetate-acrylic acid esters; hydrolyzed copolymers of acrylonitrile or acrylamide, or crosslinked polymers of these hydrolyzed copolymers; modified polymers of carboxyl-group-containing crosslinked polyvinyl alcohols; and crosslinked copolymers of isobutylene-maleic anhydride. However, favorably used is the partially-neutralized polymers of poly(acrylic acids) which is obtained by polymerizing and crosslinking a monomer including acrylic acid and/or its salt (neutralized product) as a main component.

On the occasion when the monomer including acrylic acid and/or its salt as a main component is used, another monomer may be used jointly therewith. This jointly usable other monomer is exemplified in such as US patents (mentioned in (3) below) and EP patents. Examples thereof include water-soluble or hydrophobic unsaturated monomers such as methacrylic acid, (anhydrous) maleic acid, fumaric acid, crotonic acid, itaconic acid, vinylsulfonic acid, 2-(meth)acrylamido-2-methylpropanesulfonic acid, (meth)acryloxyalkanesulfonic acids, and their alkaline metal salts and ammonium salts, and further, N-vinyl-2-pyrrolidone, N-vinylacetamide, (meth)acrylamide, N-isopropyl(meth)acrylamide, N,N-dimethyl(meth)acrylamide, 2-hydroxyethyl (meth)acrylate, methoxypolyethylene glycol (meth)acrylate, polyethylene glycol (meth)acrylate, isobutylene, and lauryl (meth)acrylate.

On the occasion when the monomer other than acrylic acid (salt) is used, this monomer other than acrylic acid (salt) is favorably in the range of 0 to 30 mol %, more favorably 0 to 10 mol %, in ratio to the total amount of the acrylic acid and/or its salt being used as a main component. Then, the absorption properties of the water-absorbent resin (composition) to finally be obtained are still more enhanced, and further, the water-absorbent resin (composition) can be obtained at still lower costs.

The water-absorbent resin has essentially a crosslinked structure. The water-absorbent resin may be a self-crosslinked type formed without any crosslinking agent, but is preferably a water-absorbent resin obtained by copolymerization or reaction with a crosslinking agent having at least two polymerizable unsaturated groups or at least two reactive groups per molecule (internal-crosslinking agent for water-absorbent resins).

Specific examples of these internal-crosslinking agents include N,N'-methylenebis(meth)acrylamide, (poly)ethylene glycol di(meth)acrylate, (poly)propylene glycol di(meth) acrylate, trimethylolpropane tri(meth)acrylate, glycerol tri(meth)acrylate, glycerol acrylate methacrylate, ethylene-oxide-modified trimethylolpropane tri(meth)acrylate, pentaerythritol hexa(meth)acrylate, triallyl, cyanurate, triallyl isocyanurate, triallyl phosphate, triallylamine, poly(meth) allyloxyalkanes, (poly)ethylene glycol diglycidyl ether, glycerol diglycidyl ether, ethylene glycol, polyethylene glycol, propylene glycol, glycerol, pentaerythritol, ethylenediamine, ethylene carbonate, propylene carbonate, polyethylenimine, and glycidyl (meth)acrylate.

These internal-crosslinking agents may be used either alone respectively or in appropriate combinations with each other. In addition, these internal-crosslinking agents may be added to the reaction system either all at once or divisionwise. On the occasion when at least one or more kinds of internal-crosslinking agents are used, it is favorable, in view of such as absorption properties of the water-absorbent resin or water-absorbent resin composition to finally be obtained, that the compound having at least two polymerizable unsaturated groups is essentially used during the polymerization.

The amount of these internal-crosslinking agents being used is set favorably in the range of 0.001 to 2 mol %, more favorably 0.005 to 1 mol %, still more favorably 0.005 to 0.5 mol %, yet still more favorably 0.01 to 0.5 mol %, yet still more favorably 6.01 to 0.2 mol %, particularly favorably 0.03 to 0.2 mol %, most favorably 0.03 to 0.15 mol %, relative to the aforementioned monomers (except for the crosslinking agent). In cases where the amount of the above internal-crosslinking agents being used is smaller than 0.001 mol % and where this amount is larger than 2 mol %, there is a possibility that sufficient absorption properties cannot be obtained, for example, the water-extractable component content may increase, or the water absorption capacity may lower.

On the occasion when the above internal-crosslinking agent is used to introduce the crosslinked structure into the inside of the polymer, it will do to add the above internal-crosslinking agent to the reaction system before or on the way of or after the polymerization of the above monomers or after the neutralization.

When the above monomers are polymerized in order to obtain the water-absorbent resin used in the present invention, it is possible to carry out bulk polymerization or precipitation polymerization. However, from the viewpoints of the performance and the polymerization control easiness and further the absorption properties of a swollen gel, it is favorable to carry out aqueous solution polymerization or reversed-phase suspension polymerization by use of the above monomers in the form of an aqueous solution.

On the occasion when the monomers are used in the form of an aqueous solution, the concentration of the monomers in this aqueous solution (hereinafter referred to as aqueous monomer solution) depends on the temperature of the aqueous solution and on the monomers, and is therefore not especially limited. However, this concentration is favorably in the range of 10 to 70 weight %, more favorably 20 to 60 weight %. In addition, when the above aqueous solution polymerization is carried out, a solvent other than water may be used jointly therewith, if necessary. The kind of this jointly usable solvent is not especially limited.

Incidentally, the reversed-phase suspension polymerization is a polymerization method in which the aqueous monomer solution is suspended in a hydrophobic organic solvent, and such a polymerization method is, for example, disclosed in US patents such as U.S. Pat. No. 4,093,776, U.S. Pat. No. 4,367,323, U.S. Pat. No. 4,446,261, U.S. Pat. No. 4,683,274, and U.S. Pat. No. 5,244,735. The aqueous solution polymerization is a polymerization method in which the aqueous monomer solution is polymerized without any dispersing solvent, and such a polymerization method is, for example, disclosed in: US patents such as U.S. Pat. No. 4,625,001, U.S. Pat. No. 4,873,299, U.S. Pat. No. 4,286,082, U.S. Pat. No. 4,973,632, U.S. Pat. No. 4,985,518, U.S. Pat. No. 5,124,416, U.S. Pat. No. 5,250,640, U.S. Pat. No. 5,264,495, U.S. Pat. No. 5,145,906, and U.S. Pat. No. 5,380,808; and European patents such as EP 0811636, EP 0955086, and EP 0922717. Such as monomers and initiators exemplified for these polymerization methods are also applicable to the present invention.

When the above polymerization is initiated, there can be used, for example, the following: radical polymerization initiators such as potassium persulfate, ammonium persulfate, sodium persulfate, t-butyl hydroperoxide, hydrogen peroxide, and 2,2'-azobis(2-amidinopropane) dihydrochloride; and photoinitiators such as 2-hydroxy-2-methyl-1-phenyl-propan-1-one. From the physical property aspect, the amount of these polymerization initiators being used is usually in the range of 0.001 to 2 mol %, favorably 0.01 to 0.1 mol % (relative to the entire monomers).

After the polymerization, the resultant polymer is usually a crosslinked hydrogel polymer, which is dried if necessary and usually pulverized before and/or after this drying, so that the water-absorbent resin is obtained. In addition, the drying is carried out usually in the temperature range of 60 to 250° C., favorably 100 to 220° C., more favorably 120 to 200° C. The drying time depends on the surface area and water content of the polymer and on the kind of the drier and is selected so as to give the objective water content.

The water content of the water-absorbent resin (composition) usable in the present invention (which is defined as the amount of water contained in the water-absorbent resin or water-absorbent resin composition and is measured by the drying loss at 105° C. in 3 hours) is not especially limited. However, from the physical property aspect of the resultant water-absorbent resin composition, the above water content is such that the water-absorbent resin (composition) can be a powder flowable even at room temperature, and is favorably such that the water-absorbent resin (composition) can be in a powder state having a water content of 0.1 to 40 weight %, more favorably 0.2 to 30 weight %, still more favorably 0.3 to 15 weight %, particularly favorably 0.5 to 10 weight %. Favorable particle diameters of the water-absorbent resin (composition) will be mentioned below. In the case where the water content of the water-absorbent resin is higher than 40 weight %, there is a possibility that the water absorption capacity may be low. In the case where the water content of the water-absorbent resin is lower than 0.1 weight %, there is a possibility that the liquid-sucking-up property may be low.

The water-absorbent resin obtained by the above process is favorably in the range of 8 to 50 g/g, more favorably 10 to 50 g/g, still more favorably 20 to 40 g/g, most 25 to 35 g/g, in absorption capacity without load (CRC) for a physiological saline solution without load (its measurement method is specified in the below-mentioned detailed description of Examples of some preferred embodiments). The physical properties such as this absorption capacity without load (CRC) are adjusted appropriately for the purpose. However, in the case where the absorption capacity without load is less than 8 μg or more than 50 g/g, there is a possibility that the water-absorbent resin composition according to the present invention cannot be obtained.

(2) Shape and Particle Diameters of Water-Absorbent Resin and Particulate Water-Absorbent Resin Composition:

The water-absorbent resin in the present invention and the particulate water-absorbent resin composition obtained in the present invention are adjusted to the specific particle size, for the purpose of achieving the present invention, favorably such that particles in the range of 850 to 150 μm (but not including 850 μm) (defined by sieve classification: JIS Z8801-1:2000) account for not less than 90 weight % of the entirety, more favorably such that particles in the range of 850 to 150 μm (but not including 850 μm) account for not less than 95 weight % of the entirety, and still more favorably such that particles in the range of 850 to 150 μm (but not including 850 μm) account for not less than 98 weight % of the entirety. In addition, it is favorable that particles not smaller than 300 μm account for not less than 60 weight % of the entirety.

Incidentally, hereupon, the entirety refers to the entirety of the particulate water-absorbent resin composition.

In addition, it is specified that particles not smaller than 250 μm account for favorably not less than 70 weight % (upper limit: 100 weight %), more favorably not less than 75 weight %. In addition, it is specified that the weight-average particle diameter (D50) of the water-absorbent resin or particulate water-absorbent resin composition is favorably in the range of 200 to 600 μm, more favorably 300 to 600 μm, still more favorably 300 to 500 μm, particularly favorably 350 to 450 μm. The particle diameters of the water-absorbent resin or particulate water-absorbent resin composition may be adjusted by such as agglomeration, if necessary. (Incidentally, hereinafter, the water-absorbent resin in the present invention and the particulate water-absorbent resin composition obtained in the present invention may jointly be referred to generically as water-absorbent resin (composition).)

The particle shape of the water-absorbent resin or particulate water-absorbent resin composition, obtained in the above way, is such as a spherical shape, a pulverized shape, or an irregular shape and is thus not especially limited. However, that of an irregular pulverized shape obtained via a pulverization step is favorably usable. Furthermore, its bulk density (defined by JIS K-3362: 1998) is favorably in the range of 0.40 to 0.80 g/ml, more favorably 0.50 to 0.75 g/ml, still more favorably 0.60 to 0.73 g/ml, from the viewpoint of the balance between the liquid permeability and the liquid-sucking-up property.

In addition, the water-absorbent resin or particulate water-absorbent resin composition in the present invention is favorably in the range of 0.25 to 0.45, more favorably 0.30 to 0.40, in logarithmic standard deviation (σζ) of particle size distribution. The smaller logarithmic standard deviation (σζ) of the particle size distribution shows the narrower particle size distribution. However, as to the water-absorbent resin or particulate water-absorbent resin composition in the present invention, it is important that the particle size distribution is not simply narrow, but has a certain degree of broadness. In the case where the logarithmic standard deviation (σζ) is less than 0.25, not only is there a possibility that the objective performance may not be obtained, but also unfavorably the productivity is greatly deteriorated. In the case where the logarithmic standard deviation (σζ) is more than 0.45, the particle size distribution is too broad, so there is a possibility that the objective performance may not be obtained.

Incidentally, the "particles not smaller than 300 μm", referred to in the present invention, refers to particles which remains on a JIS standard sieve of 300 μm in mesh opening size (to be measured) as a result of the classification by the below-mentioned sieve classification method. In addition, "particles smaller than 300 μm" similarly refers to particles which pass through the mesh of 300 μm in mesh opening size (to be measured) as a result of the classification by the below-mentioned sieve classification method. This is similar also as to the other mesh opening sizes. In addition, if 50 weight % of particles are classified with the mesh of 300 μm in mesh opening size, then their weight-average particle diameter (D50) is 300 μm.

Incidentally, the particle size adjustment will do if it is appropriately carried out by such as polymerization, gel pulverization (another designation: division of gel into small pieces), drying, pulverization, classification, agglomeration, or mixing of a plurality of water-absorbent resin particles.

(3) Surface-Crosslinking of Water-Absorbent Resin:

The water-absorbent resin, used for the particulate water-absorbent resin composition according to the present invention, may be such as obtained by the above crosslinking-polymerization and drying. However, a surface-crosslinked (secondarily crosslinked) one is favorable.

As crosslinking agents for carrying out the above surface-crosslinking, there are various ones. However, from the viewpoint of physical properties, generally, there are used such as: polyhydric alcohol compounds; epoxy compounds; polyamine compounds or products by their condensation with haloepoxy compounds; oxazoline compounds; mono-, di-, or polyoxazolidinone compounds; polyvalent metal salts; and alkylene carbonate compounds.

Specific examples of the surface-crosslinking agent, used in the present invention, are disclosed in such as U.S. Pat. No. 6,228,930, U.S. Pat. No. 6,071,976, and U.S. Pat. No. 6,254,990. Examples thereof include: polyhydric alcohol compounds (e.g. mono-, di-, tri-, tetra- or polyethylene glycol, 1,2-propylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, 1,2-cyclohexanedimethanol); epoxy compounds (e.g. ethylene glycol diglycidyl ether, glycidol); polyamine compounds (e.g. ethylenediamine, diethylenetriamine, triethylenetetramine, tetraethylenepentamine, pentaethylenehexamine, polyethylenimine, polyamidepolyamines); haloepoxy compounds (e.g. epichlorohydrin, epibromohydrin, α-methylepichlorohydrin); products by condensation between the above polyamine compounds and the above haloepoxy compounds; oxazolidinone compounds (e.g. 2-oxazolidinone) (U.S. Pat. No. 6,559,239); oxetane compounds; cyclic urea compounds; and alkylene carbonate compounds (e.g. ethylene carbonate) (U.S. Pat. No. 5,409,771). However, there is no especial limitation. For maximizing the effects of the present invention, it is favorable to at least use at least one member selected from the group consisting of the oxetane compounds (US Patent Publication No. 2002/72471), the cyclic urea compounds, and the polyhydric alcohols, among the above crosslinking agents, and it is more favorable to use at least one member selected from the group consisting of oxetane compounds and polyhydric alcohols having 2 to 10 carbon atoms, and it is still more favorable to use polyhydric alcohols having 3 to 8 carbon atoms.

Though depending on such as compounds being used or their combination, the amount of the surface-crosslinking agent being used is favorably in the range of 0.001 to 10 weight parts, more favorably 0.01 to 5 weight parts, relative to 100 weight parts of the water-absorbent resin.

In the present invention, water is used favorably for the surface-crosslinking. On this occasion, though depending on the water content of the water-absorbent resin being used, the amount of water being used is usually favorably in the range of 0.5 to 20 weight parts, more favorably 0.5 to 10 weight parts, relative to 100 weight parts of the water-absorbent resin. In addition, in the present invention, besides water, a hydrophilic organic solvent may be used, and its amount is favorably in the range of 0 to 10 weight parts, more favorably 0 to 5 weight parts, still more favorably 0 to 3 weight parts, relative to 100 weight parts of the water-absorbent resin.

Furthermore, in the present invention, favorable among various mixing methods is a method in which, after the surface-crosslinking agent has beforehand been mixed with water and/or the hydrophilic organic solvent if necessary, the resultant aqueous solution is sprayed or dropped to the water-absorbent resin to mix them together, and more favorable is the method in which the spraying is carried out. The size of droplets being sprayed is favorably in the range of 1 to 300 μm, more favorably 10 to 200 μm, in average particle diameter. In addition, when the mixing is carried out, a water-insoluble fine particle powder or a surfactant may be allowed to coexist within the range not hindering the effects of the present invention.

After having been mixed with the crosslinking agent, the water-absorbent resin is favorably heat-treated. As conditions when carrying out the above heating treatment, the heating temperature (defined as the heat medium temperature) is favorably in the range of 100 to 250° C., more favorably 150 to 250° C., and the heating time is favorably in the range of 1 minute to 2 hours. Favorable examples of combinations of the temperature and time are as follows: at 180° C. for 0.1 to 1.5 hours; and at 200° C. for 0.1 to 1 hour.

In addition, when the surface-crosslinking in the present invention is carried out, favorably the following tetra- or more functional polyol (B) is used or at least two thereof are jointly used.

(4) Tetra- or More Functional Polyol:

In the particulate water-absorbent resin composition according to the present invention, favorably, the tetra- or more functional polyol (B) is contained as an essential component. As the tetra- or more functional polyol (B), that of favorably 4 to 30, more favorably 4 to 20, still more favorably 4 to 10, in functionality is used, and its number of carbon atoms is favorably controlled in the range of 0.5 to 2 times, more favorably 1.0 to 1.5 times, of the functionality of the polyol. In the case where the functionality of such a polyol (B) is less than 4, the improvement of the liquid-sucking-up property is insufficient. In addition, in the case where the functionality of such a polyol (B) is more than 30, the effects of improving such as absorption capacity under load (e.g. AAP mentioned below) are low on an occasion when the polyol is used for the surface-crosslinking. Furthermore, in the case where the number of carbon atoms in the polyol deviates from the above ranges, there is a possibility that the improvement of the liquid-sucking-up property in the present invention may be insufficient.

Examples of the tetra- or more functional polyol (B) used favorably in the present invention include: polyhydric alcohols (e.g. polyglycerol, pentaerythritol); monosaccharide alcohols (e.g. meso-erythritol, xylitol, D(+)-xylose, D-sorbitol) or their optical isomers or mixtures of these optical isomers; disaccharide alcohols (e.g. maltitol, lactitol) or their optical isomers or mixtures of these optical isomers; and gluconic acid or its salts of such as sodium. As to these tetra- or more functional polyols (B), a part of its hydroxyl groups may be modified within the range where not fewer than four free hydroxyl groups remain. From the viewpoints of hydrophilicity, physical properties and safety and further from the viewpoint of coloring after the heating treatment, it is favorable to use the polyol (B) of which the hydroxyl groups are non-modified, more favorably sugar alcohols which are non-modified and sugar alcohols which are not higher than disaccharides, particularly favorably the monosaccharide alcohols, most favorably the D-sorbitol.

The amount of these tetra- or more functional polyols (B) being used is favorably in the range of 0.01 to 20 weight %, more favorably 0.1 to 10 weight %, still more favorably 0.1 to 5 weight %, particularly favorably 0.1 to 1 weight %, relative to the water-absorbent resin (A). Incidentally, these polyols (B) can be extracted from the particulate water-absorbent resin composition and can be quantified by such as liquid chromatography and gas chromatography.

Incidentally, if all hydroxyl groups in the polyol (B) reacts with acid groups of the water-absorbent resin to thus disappear, then it is difficult to obtain the effect of enhancing the liquid-sucking-up property in the present invention. Therefore, in the present invention, it is favorable that free hydroxyl groups derived from the polyol (B) are present on surfaces of the water-absorbent resin. Examples of such free hydroxyl groups include: unreacted polyol (B); and a polyol-water-absorbent resin formed by the reaction and bonding of only a part of hydroxyl groups of the polyol (B) with the water-absorbent resin.

The method for adding the tetra- or more functional polyol (B) will do if it is carried out in accordance with the method (aforementioned in (2) above) for adding the surface-crosslinking agent in surface-crosslinking the water-absorbent resin. Specifically, it will do if the tetra- or more functional polyol (B) is formed into a solution particularly, an aqueous solution), if necessary, and then dropped or sprayed to the water-absorbent resin (A) to mix them together. On this occasion, it is favorable to use the aforementioned surface-crosslinking agent (C) (more favorably the polyhydric alcohol, still more favorably the tri- or less-functional polyol having 3 to 8 carbon atoms) other than the tetra- or more functional polyol (B) jointly therewith, if necessary. The amount of the surface-crosslinking agent (C) other than the polyol (B), being used, is favorably in the range of 0 to 8 weight parts, more favorably 0.01 to 5 weight parts, still more favorably 0.1 to 3 weight parts, relative to 100 weight parts of the water-absorbent resin.

In the particulate water-absorbent resin composition according to the present invention comprising the water-absorbent resin (A) of the specific particle size and the tetra- or more functional polyol (B) of the specific particle size, it is permitted that the tetra- or more functional polyol (B) is simply added to the crosslinked hydrogel polymer resultant from the polymerization, a dried material of the crosslinked polymer, or a surface-crosslinked material of the particulate water-absorbent resin. In addition, it is also permitted that the above polyol is used as the aforementioned surface-crosslinking agent for the water-absorbent resin or jointly with this surface-crosslinking agent. However, favorably, the tetra- or more functional polyol (B) is used as the aforementioned surface-crosslinking agent for the water-absorbent resin or jointly with this surface-crosslinking agent and thereby caused to partially react with the water-absorbent resin. Among the tetra- or more functional polyols, the sugar alcohols (particularly, D-sorbitol) are very high in safety and therefore favorably used as the aforementioned surface-crosslinking agent for the water-absorbent resin or jointly with this surface-crosslinking agent.

That is to say, the process according to the present invention for production of a particulate water-absorbent resin composition is a process for production of a particulate water-absorbent resin composition including a water-absorbent resin (A) of a crosslinked structure obtained by polymerizing an acid-group-containing unsaturated monomer, wherein the water-absorbent resin (A) is such that particles in the range of 850 to 150 µm (but not including 850 µm) account for not less than 90 weight % of the entirety, and further wherein the process includes a step of mixing the water-absorbent resin (A) and a tetra- or more functional polyol (B) together.

In order to cause the polyol (B) to partially react, it will do if the reaction between the polyol (B) and the water-absorbent resin (A) is controlled by appropriately adjusting the reaction temperature and time and further, if necessary, by such as forced cooling after the reaction. If only a part of the tetra- or more functional polyol (B) is caused to react with the water-absorbent resin by such control in the surface-crosslinking (stop of the reaction on its way), then the particulate water-absorbent resin composition according to the present invention is favorably obtained. In the forced cooling after the reaction, the temperature (material temperature) of the water-absorbent resin is cooled favorably to not higher than 100° C. (as to the lower limit, favorably not lower than 5° C.) within 40 minutes, more favorably to not higher than 100° C. within 30 minutes, still more favorably to not higher than 100° C. within 10 minutes, particularly favorably to not higher than 100° C. within 5 minutes, after the reaction. That is to say, for achieving the present invention, it is favorable to carry out the heating treatment so that favorably 10 to 90%, more favorably 20 to 80%, still more favorably 30 to 70%, of the added tetra- or more functional polyol (B) or its hydroxyl groups will remain in the particulate water-absorbent resin composition.

Incidentally, the remaining amount (entire amount) and remaining ratio (%) are easily determined by quantifying an extract from the particulate water-absorbent resin composition. In addition, in the present invention, the polyol-(B)-derived hydroxyl groups existing on surfaces of the particulate water-absorbent resin are important. Therefore, the unreacted polyol (B), and the hydroxyl groups in the particulate water-absorbent resin composition formed by the reaction and bonding of only a part of hydroxyl groups of the polyol (B) with the water-absorbent resin, may be determined by titration, or the reacted and bonded hydroxyl groups and the unreacted hydroxyl groups may be confirmed by use of XPS (X-ray Photoelectron Spectroscopy). In addition, the amount of the unreacted polyol (B) may be measured by the below-mentioned liquid chromatography.

(5) Particulate Water-Absorbent Resin Composition:

The particulate water-absorbent resin composition according to the present invention is a particulate water-absorbent resin composition comprising a water-absorbent resin (A) of a crosslinked structure obtained by polymerizing an acid-group-containing unsaturated monomer, which composition has a particle size such that particles in the range of 850 to 150 µm (but not including 850 µm) account for not less than 90 weight % (upper limit: 100 weight %) of the entirety.

The water-absorbent resin (A) accounts for favorably not less than 80 weight % (upper limit: 100 weight %), more favorably not less than 90 weight %, still more favorably not less than 95 weight %, particularly favorably not less than 98 weight %, of the composition.

The particle size of the aforementioned composition is favorably such that particles not smaller than 250 μm account for not less than 70 weight % (upper limit: 100 weight %) of the entirety.

The particulate water-absorbent resin composition according to the present invention, favorably, contains a tetra- or more functional polyol (B) at least on surfaces. If the tetra- or more functional polyol (B) is contained at least on surfaces, then OH groups which have not changed in form due to such as the crosslinking reaction remain to thus give the hydrophilicity, so that the wettability of the particulate water-absorbent resin composition is more exhibited. Incidentally, the aforementioned tetra- or more functional polyol (B) is as previously described herein.

That is to say, the first particulate water-absorbent resin composition according to the present invention is a particulate water-absorbent resin composition comprising a water-absorbent resin (A) of a crosslinked structure obtained by polymerizing an acid-group-containing unsaturated monomer, which composition has a particle size such that particles in the range of 850 to 150 μm (but not including 850 μm) account for not less than 90 weight % of the entirety, and which composition contains a tetra- or more functional polyol (B) at least on surfaces.

The particulate water-absorbent resin composition according to the present invention, favorably, contains a tetra- or more functional polyol (B) and a tri- or more functional polycation at least on surfaces. If the tetra- or more functional polyol (B) and the tri- or more functional polycation are contained at least on surfaces, then the wettability of the particulate water-absorbent resin composition is exhibited, and further its liquid permeability is also more exhibited. Incidentally, also in this case, the aforementioned composition favorably has a particle size such that particles in the range of 850 to 150 μm (but not including 850 μm) account for not less than 90 weight % of the entirety.

The tri- or more functional polycation is a tri- or more functional polycation selected from among high-molecular polyamines or polyvalent metals. The high-molecular polyamine is an amine compound having not fewer than three cationic groups per molecule. The tri- or more functional polycation is, favorably, water-soluble. The "water-soluble" means being soluble in an amount of favorably not less than 0.5 g, more favorably not less than 1 g, relative to 100 g of water of 25° C.

Examples of the tri- or more functional polycation include, cationic polymers (e.g. polyethylenimine, polyallylamine, polyvinylamine); and polyvalent metal salts. The weight-average molecular weight of the cationic polymer is favorably in the range of 1,000 to 1,000,000, more favorably 10,000 to 500,000. The amount of it being used depends on its combination with the water-absorbent resin and/or particulate water-absorbent resin composition. However, this amount is, for example, favorably in the range of 0 to 10 weight parts, more favorably 0.001 to 8 weight parts, still more favorably 0.01 to 5 weight parts, relative to 100 weight parts of the particulate water-absorbent resin composition.

Though not especially limited, favorable examples of the tri- or more polyvalent metal include at least one metal atom selected from the group consisting of Al, Fe, Ti, Hf, Zr, and other transition metals. Above all, at least one metal atom selected from the group consisting of Al, Fe, Ti, Hf, and Zr (these have strong bondability to the carboxyl group) is more favorable, and Al and Zr are still more favorable.

That is to say, the second particulate water-absorbent resin composition according to the present invention is a particulate water-absorbent resin composition comprising a water-absorbent resin (A) of a crosslinked structure obtained by polymerizing an acid-group-containing unsaturated monomer, which composition contains a tetra- or more functional polyol (B) and a tri- or more functional polycation at least on surfaces.

In the second particulate water-absorbent resin composition according to the present invention, the content of the tri- or more polyvalent metal is favorably in the range of 0.01 to 10 weight %, more favorably 0.1 to 5.0 weight %, still more favorably 0.2 to 2.0 weight %, relative to the particulate water-absorbent resin composition.

The tri- or more polyvalent metal is free of especial limitation if it is in the range where used as a water-soluble compound. However, it is, for example, favorably used as a compound of at least one counter-anion selected from the group consisting of: inorganic compounds having $OH^-$, $CO_3^{2-}$, or $SO_4^{2-}$; organic acids (e.g. acetic acid, propionic acid); and halogens. Favorable examples of such compounds include aluminum sulfate (including hydrates), potassium aluminum sulfate, sodium aluminum sulfate, aluminum hydroxide, zirconium, acetylacetonate complex, zirconium acetate, zirconium propionate, zirconium sulfate, potassium zirconium hexafluoride, sodium zirconium hexafluoride, ammonium zirconium carbonate, potassium zirconium carbonate, and sodium zirconium carbonate. Above all, water-soluble compounds are preferable.

The tri- or more polyvalent metal may be added before the surface-crosslinking of the water-absorbent resin (A), or may be added simultaneously with the surface-crosslinking, or may be added to the particulate water-absorbent resin composition after the surface-crosslinking. Above all, it is favorable that the tri- or more polyvalent metal is added simultaneously with the surface-crosslinking or added to the particulate water-absorbent resin composition after the surface-crosslinking, and it is particularly favorable that the tri- or more polyvalent metal is added to the particulate water-absorbent resin composition after the surface-crosslinking.

The tri- or more polyvalent metal may be added in a state of a powder (powdery particles) or in a state of a slurry where the polyvalent metal is dispersed in such as water or an organic solvent. However, it is favorable that the tri- or more polyvalent metal is added in a state of a solution of the polyvalent metal, such as an aqueous solution or a solution in which the polyvalent metal is dissolved in a mixed solvent of water/the organic solvent. Though not especially limited, favorable examples of the organic solvent hereupon usable include: monohydric alcohols (e.g. isopropyl alcohol); polyhydric alcohols (e.g. propylene glycol, glycerol); acids (e.g. acetic acid, lactic acid); and organic solvents having good mixability with water (e.g. acetone, tetrahydrofuran). Furthermore, the aforementioned solution of the polyvalent metal may contain compounds of metals having a valence of less than 3 (e.g. sodium hydroxide, sodium carbonate, sodium hydrogencarbonate, sodium acetate, sodium lactate, potassium hydroxide, lithium hydroxide).

The particulate water-absorbent resin composition according to the present invention, favorably, satisfies the following relation: liquid distribution velocity (LDV) (mm/s)>−0.186× water absorption capacity without load (CRC) (g/g)+5.75 (wherein LDV>0.10 (mm/s)) and, more favorably, satisfies the following relation: liquid distribution velocity (LDV) (mm/s)>−0.186×water absorption capacity without load (CRC) (g/g)+5.85 (wherein LDV>0.10 (mm/s)) and, still more favorably, satisfies the following relation: liquid distribution velocity (LDV) (mm/s)>−0.186×water absorption capacity without load (CRC) (g/g)+5.95 (wherein LDV>0.10 (mm/s)) and, yet still more favorably, satisfies the following relation: liquid distribution velocity (LDV) (mm/s)>−0.186×water absorption capacity without load (CRC) (g/g)+6.05 (wherein LDV>0.10 (mm/s)) and, yet still more favorably, satisfies the following relation: liquid distribution velocity (LDV) (mm/s)>−0.186×water absorption capacity without load (CRC) (gig)+6.15 (wherein LDV>0.10 (mm/s)) and, particularly favorably, satisfies the following relation: liquid distribution velocity (LDV) (mm/s)>−0.195×water absorption capacity without load (CRC) (g/g)+6.45 (wherein LDV>0.10 (mm/s)).

The liquid distribution velocity (LDV) is a parameter indicating the "liquid-sucking-up property" measured by a measurement method described in the below-mentioned detailed description of Examples of some preferred embodiments. In respect to the performance enhancement of the absorbent article (e.g. disposable diaper, sanitary napkin) or absorbent structure, the water absorption capacity without load (CRC) is mainly relevant to the amount of the liquid absorbed by the absorbent article or by the absorbent structure and, on the other hand, the liquid distribution velocity (LDV) is mainly relevant to the rate at which the liquid is distributed (particularly, the initial rate at which the liquid is absorbed) in the absorbent article or in the absorbent structure. By satisfying the following relation: liquid distribution velocity (LDV) (mm/s)>−0.186×water absorption capacity without load (CRC) (g/g)+5.75 (wherein LDV>0.10 (mm/s)), the particulate water-absorbent resin composition becomes an enhanced one in both of the "liquid permeability" and "liquid-sucking-up property" (which have hitherto been antithetical physical properties) of the water-absorbent resin, so that the wettability of the particulate water-absorbent resin composition is more exhibited. In addition, there can be obtained an absorbent article or absorbent structure which is more excellent in the liquid absorption amount and the initial liquid absorption rate than conventional ones.

That is to say, the third particulate water-absorbent resin composition according to the present invention is a particulate water-absorbent resin composition comprising a water-absorbent resin (A) of a crosslinked structure obtained by polymerizing an acid-group-containing unsaturated monomer, which composition has a particle size such that particles in the range of 850 to 150 µm (but not including 850 µm) account for not less than 90 weight % of the entirety, and which composition satisfies the following relation: liquid distribution velocity (LDV) (mm/s)>−0.186×water absorption capacity without load (CRC) (g/g)+5.75 (wherein LDV>0.10 (mm/s)).

The particulate water-absorbent resin composition according to the present invention is favorably in the range of 0.03 to 0.15 in surface OH/C ratio as determined by photoelectron spectrometry. More favorably, the surface OH/C ratio as determined by photoelectron spectrometry is in the range of 0.035 to 0.12, still more favorably 0.04 to 0.1, particularly favorably 0.045 to 0.1.

The surface OH/C ratio as determined by photoelectron spectrometry is a surface OH/C ratio as measured by a measurement method described in the below-mentioned detailed description of Examples of some preferred embodiments, and is a surface OH/C ratio as determined by photoelectron spectroscopy after having washed the surfaces of the particulate water-absorbent resin composition with a non-water-soluble solvent, a water-soluble solvent, and water (physiological saline solution). In other words, it is a ratio between the OH group and C (carbon element) which exist in a compound (compound which is not washed away by the washing) fixed on the surfaces of the particulate water-absorbent resin composition favorably by covalent bonding or ionic bonding, more favorably by covalent bonding. Usually, OH groups fixed by the surface-crosslinking or surface reaction are quantified. When the surface OH/C (existing on surfaces of the particulate water-absorbent resin composition) ratio as determined by photoelectron spectroscopy is in the range of 0.03 to 0.15, the wettability of the particulate water-absorbent resin composition is favorably exhibited. In addition, the OH/C ratio (as determined by photoelectron spectroscopy) inside the particles of the particulate water-absorbent resin composition is favorably in the range of 0.000 to 0.025, more favorably 0.000 to 0.023, still more favorably 0.000 to 0.020. In the case where the OH/C ratio (as determined by photoelectron spectroscopy) inside the particles of the particulate water-absorbent resin composition is more than 0.025, there is a possibility that the liquid permeability may be inferior. The OH/C ratio inside the particles of the particulate water-absorbent resin composition can easily be determined by pulverizing the particulate water-absorbent resin composition with such as a hammer and then analyzing the inside of the particulate water-absorbent resin composition by photoelectron spectroscopy.

That is to say, the fourth particulate water-absorbent resin composition according to the present invention is a particulate water-absorbent resin composition comprising a water-absorbent resin (A) of a crosslinked structure obtained by polymerizing an acid-group-containing unsaturated monomer, which composition has a particle size such that particles in the range of 85 to 150 µm (but not including 850 µm) account for not less than 90 weight % of the entirety, and which composition is in the range of 0.03 to 0.15 in surface OH/C ratio as determined by photoelectron spectrometry.

The above third and fourth particulate water-absorbent resin compositions according to the present invention can be achieved, for example, by the above first and second particulate water-absorbent resin compositions according to the present invention. However, the above novel parameters (relative expressions) may be controlled by another method (e.g. by use of another hydrophilizing agent) so as to satisfy the third and fourth particulate water-absorbent resin compositions according to the present invention. The above third or fourth particulate water-absorbent resin composition according to the present invention is not limited to the above first or second particulate water-absorbent resin composition according to the present invention. The present inventors have completed the third and fourth particulate water-absorbent resin compositions according to the present invention by finding out that the constitution of satisfying the above parameters (relative expressions) according to the present invention provides excellent diapers and excellent effects.

In addition, the particulate water-absorbent resin composition according to the present invention, favorably, satisfies the below-mentioned conditions as to the following: the water absorption capacity without load (CRC: Centrifuge Retention Capacity) for a 0.90 weight % physiological saline solution in 30 minutes; the water absorption capacity under load (AAP: Absorbency Against Pressure) for a 0.90 weight % physiological saline solution in 60 minutes (wherein the load is 4.9 kPa); the saline flow conductivity (SFC); and the liquid-sucking-up rate (WR: Wicking Rate). Incidentally, in the present invention, the term "water absorption capacity" is a synonym of the term "absorption capacity".

That is to say, the particulate water-absorbent resin composition according to the present invention is favorably in the following ranges: not less than (8 to 20) g/g in water absorption capacity without load (CRC); not less than (8 to 20) g/g in water absorption capacity under load (AAP); not less than 10 (unit: $10^{-7} \times cm^3 \times s \times g^{-1}$) in saline flow conductivity (SFC); and not more than 180 s in liquid-sucking-up rate (WR).

The CRC is more favorably in the range of 25 to 50 µg, still more favorably 27 to 40 g/g, particularly favorably 28 to 35 g/g.

The AAP is more favorably in the range of 23 to 40 g/g, still more favorably 24 to 40 g/g, particularly favorably 25 to 40 µg, most favorably 25 to 30 µg.

The SFC is more favorably not less than 20, still more favorably not less than 30, particularly favorably not less than 40, most favorably not less than 50.

The WR is more favorably in the range of 2 to 120 s, still more favorably 5 to 90 s, particularly favorably 5 to 80 s, most favorably 5 to 70 s.

The CRC, AAP, SFC, and WR are parameters of water-absorbent resins favorable for cases where they are used for diapers. It is favorable, from the viewpoints of high absorption and low leakage in practical use, that the above parameters are controlled in the above ranges. These physical properties are obtained by appropriately adjusting the production conditions (e.g. adjusting the crosslinking density in the polymerization or surface-crosslinking) in the aforementioned production process.

In the case where the water absorption capacity without load (CRC) is less than (8 to 20) g/g, problems of such as leakage and skin eruption are caused in practical use for disposable diapers on occasions of uses for the below-mentioned absorbent structure and/or absorbent article (e.g. disposable diaper).

In the cases where the water absorption capacity under load (AAP) is less than (8 to 20) g/g and where the saline flow conductivity (SFC) is less than 10 (unit: $10^{-7} \times cm^3 \times s \times g^{-1}$), if a load such as body weight is applied to the particulate water-absorbent resin composition, then the liquid distribution and the liquid absorption force are so inferior that: in the absorbent structure and/or absorbent article, the liquid distribution is not done, but the liquid blocking occurs to thus cause the problems of such as leakage and skin eruption in practical use for disposable diapers.

In the case where the liquid-sucking-up rate (WR) is more than 180 s, it is not appropriate for practical use for diapers, because, in practical use, the liquid (water) cannot be sucked up to the entire surfaces or top surface of the diapers in the diapers worn along buttocks.

In addition, the liquid permeability and the liquid-sucking-up property have hitherto been antithetical physical properties, whereas, as to the particulate water-absorbent resin composition according to the present invention, there is obtained a particulate water-absorbent resin composition enhanced in both with good balance, and the liquid-sucking-up rate (WR) is very fast in comparison with the AAP and the SFC.

That is to say, the balance between the liquid permeability and liquid-sucking-up property of the particulate water-absorbent resin composition is expressed by liquid permeation sucking-up efficiency defined as liquid permeability/liquid-sucking-up rate, that is, SFC (unit: $10^{-7} \times cm^3 \times s \times g^{-1}$)/WR (s). The particulate water-absorbent resin composition according to the present invention is, in liquid permeation sucking-up efficiency (SFC/WR), favorably not less than 0.50 (unit: $10^{-7} \times cm^3 \times g^{-1}$) and not more than 100 (unit: $10^{-7} \times cm^3 \times g^{-1}$), more favorably not less than 0.70 (unit: $10^{-7} \times cm^3 \times g^{-1}$) and not more than 100 (unit: $10^{-7} \times cm^3 \times g^{-1}$), particularly favorably not less than 1.00 (unit: $10^{-7} \times cm^3 \times g^{-1}$) and not more than 100 (unit: $10^{-7} \times cm^3 \times g^{-1}$), and thus much higher than conventional ones (around 0.4 (unit: $10^{-7} \times cm^3 \times g^{-1}$)). Therefore, this composition is so excellent in the balance between the liquid permeability and liquid-sucking-up property as to be favorable for sanitary materials.

In addition, the particulate water-absorbent resin composition according to the present invention is excellent also in the balance between the water absorption capacity without load and the liquid-sucking-up property, and this balance is expressed by capacity-without-load sucking-up efficiency defined as water absorption capacity without load/liquid-sucking-up rate, that is, CRC (g/g)/WR (s). The particulate water-absorbent resin composition according to the present invention is, in capacity-without-load sucking-up efficiency (CRC/WR), favorably not less than 0.15 (g/g/s) and not more than 2 (g/g/s), more favorably not less than 0.20 (g/g/s) and not more than 2 (g/g/s), particularly favorably not less than 0.25 (g/g/s) and not more than 2 (g/g/s), and thus much higher than conventional ones (around 0.1 (g/g/s)). Therefore, this composition is so excellent in the balance between the water absorption capacity without load and the liquid-sucking-up property as to be favorable for sanitary materials.

In addition, the particulate water-absorbent resin composition according to the present invention is excellent also in the balance between the water absorption capacity under load and the liquid-sucking-up property, and this balance is expressed by capacity-under-load sucking-up efficiency defined as water absorption capacity under load/liquid-sucking-up rate, that is, AAP (g/g)/WR (s). The particulate water-absorbent resin composition according to the present invention is, in capacity-under-load sucking-up efficiency (AAP/WR), favorably not less than 0.15 (g/g/s) and not more than 2 (g/g/s), more favorably not less than 0.20 (g/g/s) and not more than 2 (g/g/s), particularly favorably not less than 0.25 (g/g/s) and not more than 2 (g/g/s), and thus much higher than conventional ones (around 0.1 (g/g/s)). Therefore, this composition is so excellent in the balance between the water absorption capacity under load and the liquid-sucking-up property as to be favorable for sanitary materials.

Such as shape and water-extractable component content of the particulate water-absorbent resin composition according to the present invention are also in the aforementioned ranges, and its water-extractable component content is defined as favorably not higher than 25 weight % (lower limit: 0 weight %), more favorably not higher than 20 weight %, still more favorably not higher than 15 weight %. In addition, the water content of the particulate water-absorbent resin composition according to the present invention is favorably in the range of 0.1 to 5 weight %, more favorably 0.1 to 3 weight %, still more favorably 0.2 to 2 weight %, relative to the particulate water-absorbent resin composition. In the case where the water content is higher than 5 weight %, there is a possibility that the water absorption capacity may be deteriorated. In the case where the water content is lower than 0.1 weight %, there is a possibility that the liquid distribution velocity may be slow. In addition, the colored state of the particulate water-absorbent resin composition according to the present invention is favorably in the range of 0 to 15, more favorably 0 to 13, still more favorably 0 to 10, particularly favorably 0 to 5, in YI value (Yellow Index/refer to EP 0942014 and EP 1108745). Furthermore, its residual monomer content is also favorably in the range of 0 to 400 ppm, more favorably 0 to 300 ppm.

(6) Third Component of Particulate Water-Absorbent Resin Composition:

Various inorganic powders (D) may further be added, as third components, to the water-absorbent resin and/or the particulate water-absorbent resin composition. However, these are added favorably within the range not decreasing the liquid-sucking-up rate (liquid distribution velocity).

Specific examples of the inorganic powders (D) being used include: metal oxides (e.g. silicon dioxide, titanium oxide); silicic acid (salts) (e.g. natural zeolite, synthetic zeolite); kaolin; talc; clay; and bentonite. Favorable are silicon dioxide and silicic acid (salts) of not larger than 200 μm in average particle diameter measured by the Coulter Counter Method.

As to the method for mixing the inorganic powder (D) and the particulate water-absorbent resin composition together, if the inorganic powder (D) is in the form of solid particles, then such as a dry blending method (in which a powder is mixed with another powder) and a wet mixing method can be adopted. However, in the case where a powder is mixed with another powder, there is a possibility that the particulate water-absorbent resin composition may not uniformly be mixed with the inorganic powder (D), or that the adhesion or bonding between the inorganic powder (D) and the particulate water-absorbent resin composition may not be sufficient. In the case where the particulate water-absorbent resin composition obtained in this way is used for absorbent articles (e.g. diapers), there is an unfavorable possibility that it may be difficult to obtain uniform-performance absorbent articles (e.g. diapers), because of separation and segregation of the particulate water-absorbent resin composition and the inorganic powder (D) from each other in such as production processes for the absorbent articles. Such a phenomenon is, for example, recognized also from a great difference between a value given by measuring the liquid distribution velocity (LDV) with the particle size of the particulate water-absorbent resin composition left as it is (Bulk) and a value given by measuring the liquid distribution velocity (LDV) with the particle size of the particulate water-absorbent resin composition classified in the range of 500 to 300 μm.

If the inorganic powder (D) is in the form of solid particles, then the amount of it being used is, for example, favorably in the range of 0 to 0.5 weight part, more favorably 0 to 0.3 weight part, still more favorably 0 to 0.1 weight part, particularly favorably 0 to 0.05 weight part, relative to 100 weight parts of the particulate water-absorbent resin composition, though depending on the combination with the water-absorbent resin and/or water-absorbent resin composition. In the case where the amount of the inorganic powder (D) in the form of solid particles, being added, is larger than 0.5 weight part, there is an unfavorable possibility that it may be difficult to obtain the aforementioned uniform-performance water-absorbent articles (e.g. diapers).

In addition, in the particulate water-absorbent resin composition and its production process according to the present invention, the following materials may further be added, if necessary, to the water-absorbent resin and/or the particulate water-absorbent resin composition within the range not lowering the liquid-sucking-up rate (liquid distribution velocity) (e.g. in an amount of about 0 to about 10 weight parts relative to 100 weight parts of the water-absorbent resin and/or the particulate water-absorbent resin composition), such as: deodorants; antibacterial agents; perfumes; foaming agents; pigments; dyes; plasticizers; pressure-sensitive adhesives; surfactants; manure; oxidants; reducing agents; water; salts; chelating agents; fungicides; hydrophilic polymers (e.g. polyethylene glycol); paraffins; hydrophobic polymers; thermoplastic resins (e.g. polyethylene, polypropylene); and thermosetting resins (e.g. polyester resins, urea resins).

(7) Uses, and Absorbent Structure and/or Absorbent Article:

The particulate water-absorbent resin composition according to the present invention is excellent in the hygroscopic property and can widely be used for uses of conventional water-absorbent resins, such as: agriculture and horticulture; cable-sealing agents; public works and buildings; and foods. However, because this composition combines the liquid permeability and the liquid-sucking-up property which are physical properties necessary for absorbent articles (e.g. diapers), this composition is used favorably as a solidifying agent (absorbing and gelling agent) for urine, excrement, or blood.

Because the particulate water-absorbent resin composition according to the present invention is particulate, usually a material containing this composition is molded and then used as an absorbent structure. In the present invention, the absorbent structure is favorably in the range of 20 to 100 weight %, more favorably 30 to 100 weight %, still more favorably 30 to 90 weight %, particularly favorably 40 to 80 weight %, in particulate water-absorbent resin composition content (core concentration) relative to the total weight of the particulate water-absorbent resin composition and hydrophilic fibers. In the case where the core concentration is less than 20 weight %, the properties of the particulate water-absorbent resin composition are difficult to make good use of.

Incidentally, an example of preferred embodiments of the use of the particulate water-absorbent resin composition according to the present invention in absorbent structures is application to a water-absorbent composite of expansion anisotropy (expandability in the thickness directions) illustrated in U.S. Pat. No. 5,853,867. If the particulate water-absorbent resin composition according to the present invention, which is excellent in the distributability, is used, then there are advantages in that there can be obtained an absorbent structure greatly improved not only as to the expansion in the thickness directions, but also as to the liquid distribution in the sideways (horizontal) directions.

Such an absorbent structure is favorably compression-molded so as to be in the range of 0.06 to 0.50 g/cc in density and in the range of 0.01 to 0.20 $g/cm^2$ in basis weight. Incidentally, examples of fibrous materials being used include hydrophilic fibers, such as pulverized wood pulp and besides, cotton linters, crosslinked cellulose fibers, rayon, cotton, wool, acetate, and vinylon. Favorable are air-laid materials of them.

Furthermore, the absorbent article in the present invention is, for example, an absorbent article comprising the above absorbent structure in the present invention, a liquid-permeable surface sheet, and a liquid-impermeable back sheet. Specific examples of the absorbent article include sanitary materials such as adult disposable diapers being developed greatly in recent years, and besides, children's diapers, sanitary napkins, and what is called incontinent pads.

DETAILED DESCRIPTION OF THE PREFERRED EMBODIMENTS

Hereinafter, the present invention is more specifically illustrated by the following Examples of some preferred embodiments in comparison with Comparative Examples not according to the present invention. However, the present invention is not limited to these Examples.

Incidentally, when the measurement methods described herein are applied to the water-absorbent resin or particulate water-absorbent resin composition separated from absorbent articles (e.g. diapers), it is favorable to measure the water-absorbent resin or particulate water-absorbent resin composition after having adjusted its water content to not higher than 5 weight % by such as drying it with a vacuum drier (temperature-adjusted to 60° C.) for not less than 16 hours.

In addition, unless otherwise noted, the following tests were measured under an atmosphere of 1 atm, 25±2° C. and a relative humidity of 30 to 50% RH and were carried out in the range of 25±2° C. also in liquid temperature being used.

<Measurement of Water Content>:

An amount of 1 g of particulate water-absorbent resin composition was placed into an aluminum-made cup of 4 cm in bottom diameter and 2 cm in height in a way of being spread uniformly on the bottom of the aluminum-made cup. Then, this cup was left in a hot-air drier (temperature-adjusted to 105° C.) for 3 hours to calculate the water content (%) of the particulate water-absorbent resin composition from the weight loss on drying.

<Water Absorption Capacity without Load (CRC)>:

An amount of 0.200 g of water-absorbent resin (or particulate water-absorbent resin composition) was uniformly placed into a nonwoven-fabric-made bag (trade name: Heatron Paper, type: GSP-22, produced by Nangoku Pulp Kogyo Co., Ltd.) (60 mm×60 mm) and then immersed into a 0.9 weight % physiological saline solution (aqueous sodium chloride solution) of which the temperature had been adjusted to 25° C. After 30 minutes, the bag was pulled up and then drained of water by a centrifugal force of 250 cm/sec$^2$ (250 G) with a centrifugal separator (produced by Kokusan Co., Ltd., centrifugal separator, model: H-122) for 3 minutes, and then the weight W1 (g) of the bag was measured. In addition, the same procedure as the above was carried out without the water-absorbent resin (or particulate water-absorbent resin composition), and the resultant weight W0 (g) was measured. Then, the water absorption capacity (g/g) without load was calculated from these W1 and W0 in accordance with the following equation:

Water absorption capacity (g/g) without Load=[($W1$ (g)−$W0$ (g))/weight (g) of water-absorbent resin (or particulate water-absorbent resin composition)]−1

<Water Absorption Capacity Under Load (AAP)>:

A stainless metal gauze, which was a screen of 400 meshes (mesh opening size: 38 μm), was attached by fusion to a bottom of a plastic supporting cylinder having an inner diameter of 60 mm. Then, onto the above metal gauze, there was uniformly spread 0.900 g of water-absorbent resin (or particulate water-absorbent resin composition), and further thereon, there were mounted a piston and a load in sequence, wherein the piston had an outer diameter of only a little smaller than 60 mm and made no gap with the supporting cylinder, but was not hindered from moving up and down, and wherein the piston and the load were adjusted so that a load of 4.83 kPa (0.7 psi) could uniformly be applied to the water-absorbent resin (or particulate water-absorbent resin composition). Then, the weight Wa (g) of the resultant one set of measurement apparatus was measured.

A glass filter plate having a diameter of 90 mm (produced by Sogo Rikagaku Glass Seisakusho Co., Ltd., pore diameter: 100 to 120 μm) was mounted inside a Petri dish having a diameter of 150 mm, and then a 0.90 weight % physiological saline solution was added up to the same level as the top surface of the glass filter plate, on which a filter paper having a diameter of 90 mm (produced by Toyo Filter Paper Co., Ltd., ADVANTEC; No. 2) was then mounted so that its entire surface would be wetted, and further, an excess of liquid was removed.

The above one set of measurement apparatus was mounted on the above wet filter paper, thereby getting the liquid absorbed under the load. Then, 1 hour later, the one set of measurement apparatus was removed by being lifted to measure its weight Wb (g). Then, the water absorption capacity (g/g) under load was calculated from the Wa and Wb in accordance with the following equation:

Water absorption capacity (g/g) under load=($Wb$ (g)−$Wa$ (g))/weight((0.9) g) of water-absorbent resin (or particulate water-absorbent resin composition)

<Saline Flow Conductivity (SFC)>:

The following test was carried out according to the saline flow conductivity (SFC) test as described in JP-A-509591/1997 (Kohyo).

An apparatus as shown in FIG. 1 was used, and a particulate water-absorbent resin composition (0.900 g) as uniformly placed in a receptacle 40 was swollen in synthetic urine (1) under a load of 0.3 psi (2.07 kPa) for 60 minutes (which was 120 minutes in the case of measuring the retention ratio of the saline flow conductivity (SFC)), and the gel layer height of the resultant gel 44 was recorded. Next, under the load of 0.3 psi (2.07 kPa), a 0.69 weight % aqueous sodium chloride solution 33 was passed through the swollen gel layer from a tank 31 under a constant hydrostatic pressure.

The amount of the liquid passing through the gel layer was recorded as a function to time with a computer and a balance at twenty seconds' intervals for 10 minutes. The rate $F_s$ (t) of the flow passing through the swollen gel 44 (mainly between particles thereof) was determined in a unit of g/s by dividing the incremental weight (g) by the incremental time (s). The time when the constant hydrostatic pressure and the stable flow rate had been obtained was represented by $t_s$, and only the data as obtained between $t_s$ and 10 minutes were used for the flow rate calculation. The $F_s$ (t=0) value, namely, the initial rate of the flow passing through the gel layer, was calculated from the flow rates as obtained between $t_s$ and 10 minutes. The $F_s$ (t=0) was calculated by extrapolating the results of a least-squares fit of $F_s$ (t) versus time to t=0.

Saline flow conductivity=$(F_s(t=0) \times L_0)/(\rho \times A \times \Delta P)$=

$(F_s(t=0) \times L_0)/139{,}506$ where:

$F_s$ (t=0): flow rate denoted by g/s;

$L_0$: initial thickness of gel layer denoted by cm;

$\rho$: density of NaCl solution (1.003 g/cm$^3$);

A: area of top of gel layer in cell 41 (28.27 cm$^2$);

$\Delta P$: hydrostatic pressure applied to gel layer (4,920 dyne/cm$^2$); and the unit of the saline flow conductivity (SFC) is: ($10^{-7} \times$ cm$^3 \times$ s$\times$g$^{-1}$).

As to the apparatus as shown in FIG. 1, a glass tube 32 was inserted in the tank 31, and the lower end of the glass tube 32 was placed so that the 0.69 weight % aqueous sodium chloride solution 33 could be maintained at a height of 5 cm from the bottom of the swollen gel 44 in the cell 41. The 0.69 weight % aqueous sodium chloride solution 33 in the tank 31 was supplied to the cell 41 through an L-tube 34 having a cock. A receptacle 48 to collect the passed liquid was placed under the cell 41, and this collecting receptacle 48 was set on a balance 49. The inner diameter of the cell 41 was 6 cm, and a No. 400 stainless metal gauze (mesh opening size: 38 μm) 42 was set at the bottom thereof. Holes 47 sufficient for the liquid to pass through were opened in the lower portion of a piston 46, and its bottom portion was equipped with a well-permeable glass filter 45 so that the water-absorbent resin composition or its swollen gel would not enter the holes 47.

The cell 41 was placed on a stand to put the cell thereon. The face, contacting with the cell, of the stand was set on a stainless metal gauze 43 that did not inhibit the liquid permeation.

The synthetic urine (1) as used was obtained by mixing together the following: 0.25 g of calcium chloride dihydrate; 2.0 g of potassium chloride; 0.50 g of magnesium chloride hexahydrate; 2.0 g of sodium sulfate; 0.85 g of ammonium dihydrogenphosphate; 0.15 g of diammonium hydrogenphosphate; and 994.25 g of pure water.

<Extractable Component Content>:

Into a plastic receptacle of 250 ml in capacity (diameter 6 cm×height 9 cm) having a lid, 184.3 g of 0.900 weight % aqueous sodium chloride solution was weighed out. Then, 1.00 g of (particulate) water-absorbent resin (composition) was added to this aqueous solution, and they were stirred at a revolution rate of 500 rpm with a magnetic stirring rod of 8 mm in diameter and 25 mm in length for 16 hours, whereby extractable components were extracted from the resin. The resultant extract liquid was filtrated with a filter paper (produced by ADVANTEC Toyo Co., Ltd., trade name: JIS P 3801, No. 2, thickness: 0.26 mm, diameter of captured particles: 5 μm), and then 50.0 g of the resultant filtrate was weighed out and used as a measuring solution.

To begin with, only the 0.900 weight % aqueous sodium chloride solution was firstly titrated with an aqueous 0.1N NaOH solution until the pH reached 10, and then the resultant solution was titrated with an aqueous 0.1N HCl solution until the pH reached 2.7, thus obtaining blank titration amounts ([bNaOH] ml and [bHCl] ml).

The same titration procedure was carried out also for the measuring solution, thus determining titration amounts ([NaOH] ml and [HCl] ml).

For example, if the water-absorbent resin comprises acrylic acid and its sodium salt in known amounts, then the extractable component content of the water-absorbent resin can be calculated from the average molecular weight of the monomers and the titration amounts, as obtained from the above procedures, in accordance with the following equation. In the case of unknown amounts, the average molecular weight of the monomers was calculated from the neutralization degree as determined by the titration.

Extractable component content(weight %)=0.1×(average molecular weight)×184.3×100×([HCl]−[bHCl])/1,000/1.0/50.0

Neutralization degree(mol %)=[1−([NaOH]−[bNaOH])/([HCl]−[bHCl])]×100

Figure 2:
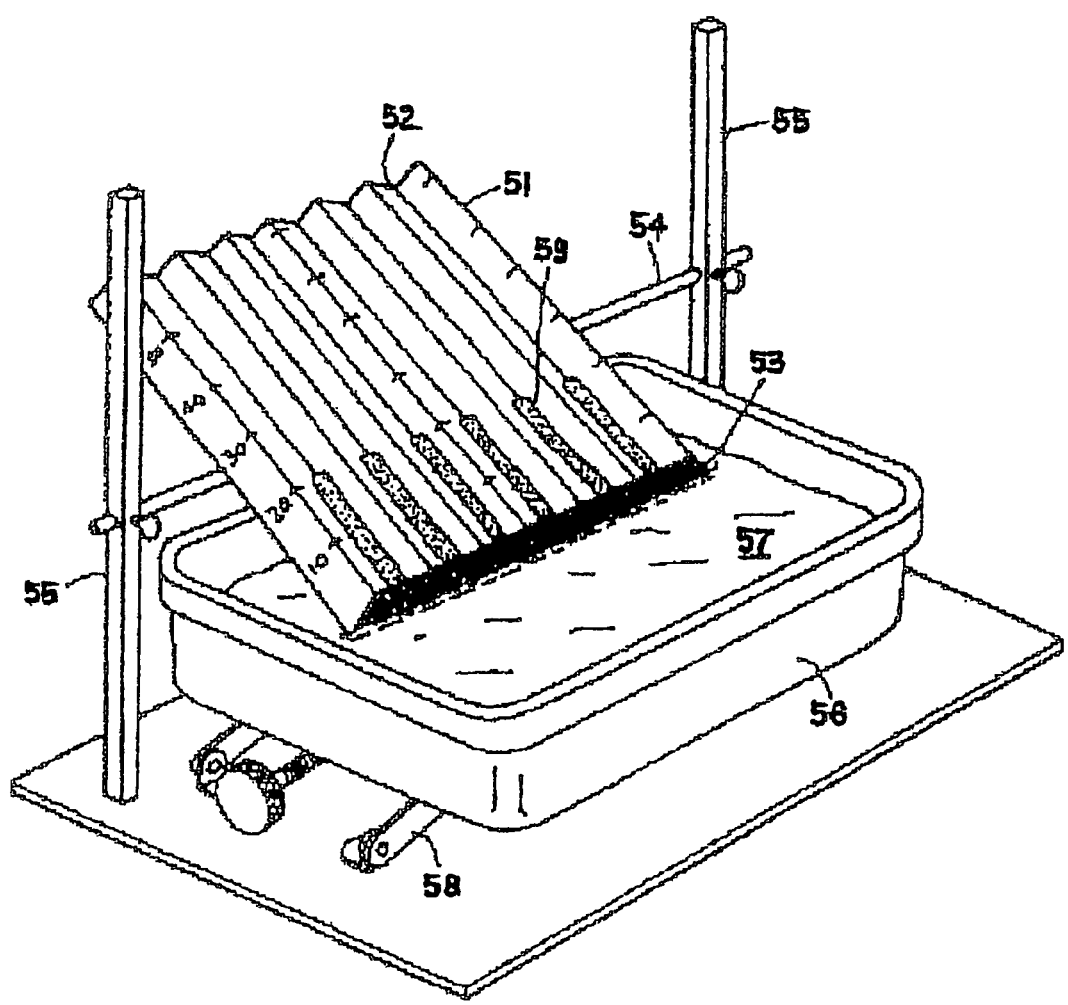
FIG. 2 is a perspective view of an apparatus as used for determining the liquid-sucking-up rate.
Figure 3:
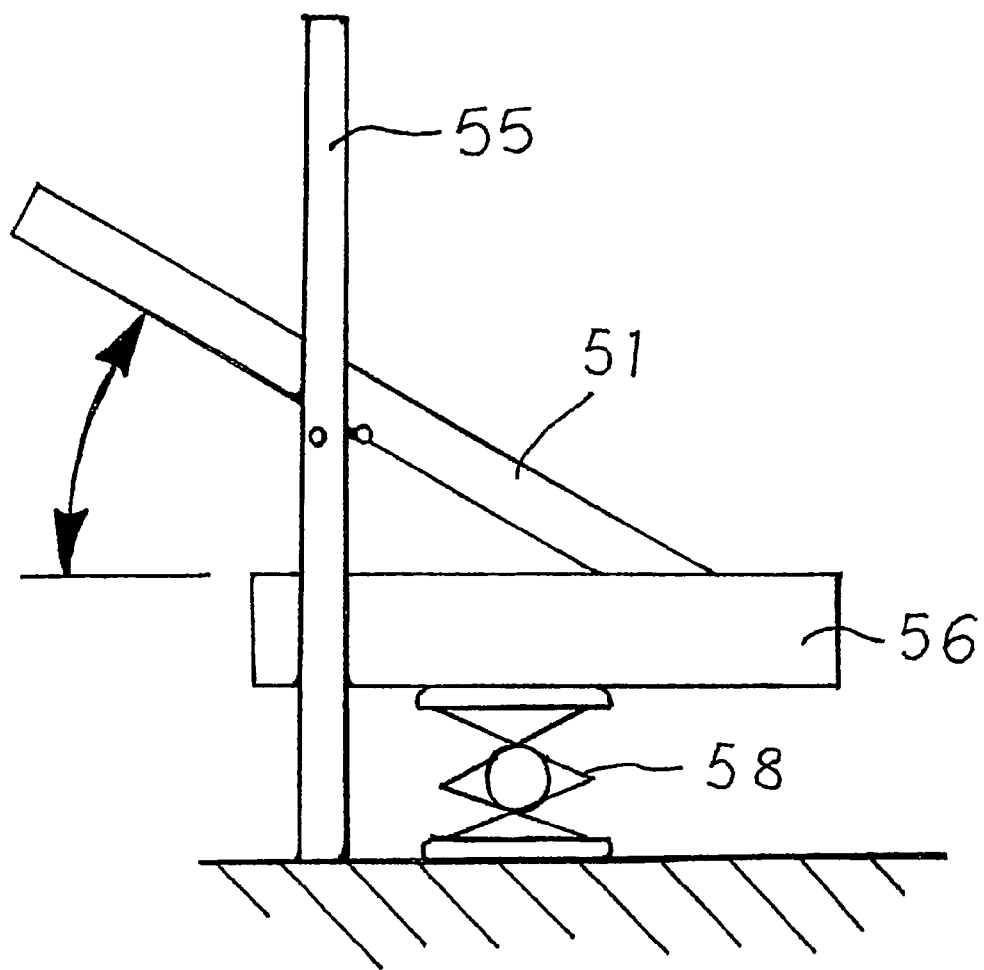
FIG. 3 is a side view of FIG. 2.

<Liquid-Sucking-Up Rate (WR) and Liquid Distribution Velocity (LDV)>:

The measurement of the liquid-sucking-up rate (WR) was carried out with a sucking-up index measurement apparatus (FIGS. 2 and 3) as described in JP-A-200068/1993 (Kokai) (EP 0532002). Incidentally, the trough sheet was prepared in the SUS 304 stainless steel grade 2B finishing.

An amount of 1.00 g±0.005 g of particulate water-absorbent resin composition (having been classified in the range of 300 to 500 μm) was uniformly spread between graduations of 0 and 20 cm in trough grooves of a trough sheet (as set at an angle of 20°). Furthermore, the particulate water-absorbent resin composition was dispersed more uniformly with a spatula.

In the present measurement, it is favorable to use the particulate water-absorbent resin composition having been classified in the particle size range of 300 to 500 μm. However, for example, in the case where it is difficult to obtain the particulate water-absorbent resin composition in that particle size range, the resultant particulate water-absorbent resin composition may be measured in a state left as it is (Bulk) without being especially classified.

As the liquid being used for the liquid-sucking-up, there was used a physiological saline solution having been prepared by coloring in a ratio of 0.01 g of food blue color #1 (Tokyo Kasei Kogyo K. K.) to 1 L of 0.9 weight % physiological saline solution (aqueous sodium chloride solution).

The measurement of the liquid-sucking-up rate (WR) was initiated at the same time as the contact of the screen mesh of the stainless steel with the liquid after the surface of the liquid in a liquid reservoir tank had been adjusted so as to be 0.5 cm above the lowest position of the troughs. The liquid-sucking-up rate (WR) indicates a time (sec) for the liquid to be sucked up to a graduation position of 10 cm. Incidentally, as to the rate at which the screen mesh of the stainless steel was impregnated with the liquid in the liquid reservoir tank up to 0.5 cm above the lowest position of the troughs, this impregnation was made at a rate of 1.35 to 1.40 mm/s in the vertical direction from the liquid surface.

In addition, the liquid distribution velocity (LDV) is calculated in accordance with the following equation.

LDV (mm/s)=100 (mm)/$WR$(s)

<Weight-Average Particle Diameter>:

The water-absorbent resin (or particulate water-absorbent resin composition), having been pulverized, was classified with JIS standard sieves having mesh opening sizes of such as 850 μm, 600 μm, 500 μm, 425 μm, 300 μm, 212 μm, 150 μm, 106 μm, and 75 μm (JIS Z8801-1:2000). Then, the percentages R of the residues on these sieves were plotted on a logarithmic probability paper. Therefrom, the weight-average particle diameter (D50) was read.

<Logarithmic Standard Deviation (σζ) of Particle Size Distribution>:

The water-absorbent resin (or particulate water-absorbent resin composition) was classified with JIS standard sieves having mesh opening sizes of 850 μm, 710 μm, 600 μm, 500 μm, 425 μm, 300 μm, 212 μm, 150 μm, and 45 μm: Then, the percentages R of the residues on these sieves were plotted on a logarithmic probability paper. Thus, if X1 is defined as a particle diameter when R=84.1 weight %, and if X2 is defined as a particle diameter when R=15.9 weight %, then the logarithmic standard deviation (σζ) is shown by the following equation. The smaller σζ value shows the narrower particle size distribution.

σζ=0.5×ln(X2/X1)

As to the classification method for measuring the logarithmic standard deviation (σζ) of the particle size distribution, 10.0 g of water-absorbent resin (or particulate water-absorbent resin composition) was placed onto JIS standard sieves (having mesh opening sizes of 850 μm, 710 μm, 600 μm, 500 μm, 425 g/m, 300 μm, 212 μm, 150 μm, and 45 μm) (THE IIDA TESTING SIEVE: diameter=8 cm) and then classified with a shaking classifier (IIDA SIEVE SHAKER, TYPE: ES-65 type, SER. No. 0501) for 5 minutes.

<Polyol Content>:

An amount of 1 g of particulate water-absorbent resin composition was added to 100 g of 0.9 weight % aqueous sodium chloride solution in a beaker of 6 cm in bottom diameter under stirring (stirring at a revolution rate of 500 rpm with a magnetic stirring rod of 8 mm in diameter and 25 mm in length by a magnetic stirrer), and then they were stirred for 1 hour. Thereby a polyol which had not reacted with the particulate water-absorbent resin composition was extracted and then analyzed by liquid chromatography to determine the amount of the unreacted polyol from a beforehand prepared calibration curve. The amount of the unreacted polyol was determined as an amount (unit: ppm) per a unit amount of particulate water-absorbent resin composition.

<Photoelectron Spectroscopy (XPS: X-Ray Photoelectron Spectroscopy)>:

(Experimental Operation h1: Washing Treatment with Organic Solvent):

About 200 mg of particulate water-absorbent resin composition was placed into a 10 ml sample tube (inner diameter 18 mm×height 44 mm), and then 5 ml of cyclohexane was added thereto. A magnetic stirring rod of 4 mm in diameter and 10 mm in length was added thereto, and then the above sample tube was sealed airtightly. The materials were stirred at room temperature with a magnetic stirrer for 1 hour in a state where particles were dispersed in the entire liquid. Thereafter, the materials were decanted, and then a filter paper having been cut into strips was used to remove the cyclohexane to such a degree that no liquid residue became seen between particles clearly with the eye. After this operation had been carried out two times, the resultant particulate water-absorbent resin composition was dried at 100° C. under a reduced pressure of 100 mmHg with a vacuum drier for 2 hours, thus obtaining a particulate water-absorbent resin composition having been wash-treated with the organic solvent.

(Experimental Operation h2: Washing Treatment with Physiological Saline Solution):

About 100 mg of the organic-solvent-wash-treated particulate water-absorbent resin composition having been obtained from Experimental Operation h1 was placed into the 10 ml sample tube (inner diameter 18 mm×height 44 mm), and then 10 ml of 0.9 weight % aqueous sodium chloride solution was added thereto, and then the above sample tube was sealed airtightly. The materials were stirred with a magnetic stirrer for 1 hour in the same way as of Experimental Operation h1. Next, 4 drops (0.1 to 0.2 g) of concentrated hydrochloric acid was added thereto with a pipette under stirring, and then the stirring was stopped. The materials were decanted, and then a filter paper having been cut into strips was used to remove the liquid to such a degree that no liquid residue became seen between particles clearly with the eye. The resultant particulate water-absorbent resin composition was dried at 60° C. under about 100 mmHg for 4.5 hours and then at 100° C. under about 100 mmHg for 17 hours and then further at 100° C. under about 1 mmHg with a vacuum drier for 3 hours, thus obtaining a particulate water-absorbent resin composition having been wash-treated with the physiological saline solution.

(Experimental Operation h3: Washing Treatment with Methanol and Water):

About 50 mg of the physiological-saline-solution-wash-treated particulate water-absorbent resin composition having been obtained from Experimental Operation h2 was placed into the sample tube (inner diameter 18 mm×height 44 mm), and then 2 ml of solution (having been prepared by mixing 100 ml of methanol with 0.5 g of 36 weight % hydrochloric acid) was added thereto. Then, the above sample tube was sealed airtightly, and then the particulate water-absorbent resin composition and the above solution therein were stirred with an ultrasonic cleaner (as equipped with a vibrator of 35 kHz) for 5 minutes. Next, the materials were decanted, and then a filter paper having been cut into strips was used to remove the liquid to such a degree that no liquid residue became seen between particles clearly with the eye. This operation was carried out two times. Next, the following operation was carried out two times: 5 ml of methanol was added to the same sample tube containing the resultant particulate water-absorbent resin composition, and then the materials were stirred with the ultrasonic cleaner for 5 minutes, and then methanol was decanted, and then a filter paper having been cut into strips was used to remove the liquid to such a degree that no liquid residue became seen between particles clearly with the eye. Furthermore, the resultant particulate water-absorbent resin composition was dried, with a vacuum drier, at 90° C. under about 100 mmHg for 15 hours and then at 90° C. under about 1 mmHg for 2 hours, thus obtaining a particulate water-absorbent resin composition having been wash-treated with methanol and water.

(Experimental Operation h4: Surface Trifluoroacetation):

The methanol-and-water-wash-treated particulate water-absorbent resin composition having been obtained from Experimental Operation h3 (about 50 mg) was taken into a polypropylene-made cup (1) of 10 mm in diameter and 20 mm in height having 40 to 50 holes of 100 to 300 μm in diameter in its sides. Then, this polypropylene-made cup (1) was put on a stand of a 50 ml sample tube (inner diameter 31 mm×height 75 mm) as equipped with the stand of 10 mm in diameter and 5 mm in height in the middle of the bottom. Then, 500 μl of trifluoroacetic anhydride (TFAA) was added to the periphery of the stand in the above sample tube. Thereafter, the sample tube was sealed airtightly and then left at room temperature for 1 to 3 hours to make a reaction between the TFAA and the OH groups on surfaces of the particulate water-absorbent resin composition having been processed (surface-washed) by the experimental operations h1 to h3 (the present operation is an operation for making the liquid TFAA untouched directly with the particulate water-absorbent resin composition in the cup and making the vapor of the TFAA contact with the particulate water-absorbent resin composition to thus react therewith). Next, under the coexistence of KOH solid, the particulate water-absorbent resin composition was dried, with a vacuum drier, at 60° C. under about 100 mmHg for not less than 2 hours and then further at 60° C. under about 1 mmHg for not less than 2 hours. With the sample tube sealed airtightly, the resultant particulate water-absorbent resin composition was preserved under the coexistence of silica gel in a desiccator. Then, within 1 week, the preserved sample was subjected to the measurement as shown in Experimental Operation h5.

(Experimental Operation h5: Measurement of OH/C Ratio):

A measurement sample was prepared by uniformly spreading the particulate water-absorbent resin composition (having been obtained from Experimental Operation h4) on a sample stand of a rectangular shape of about 6 cm×about 1 cm on which an electrically conductive pressure sensitive adhesive tape (having been cut into the size about 1 cm square) was stuck. In order to obtain a spectrum of each element of carbon and fluorine, an XPS analyzer (JEOL JPS-9000MX) was used to gas-exhaust the sample in a preliminary exhaust room for not less than 3 hours, and then the sample was moved into a sample room for measurement. $MgK_\alpha$ rays were used as an excitation X-ray source, and the conditions were set at an acceleration voltage of 10 kV, an emission current of 10 mA, a pass energy of the detector of 10 eV, and an energy-sweeping interval of the detector of 0.1 eV, and the scan was repeated 10 times in number of times of the integration, whereby photoelectron spectra were obtained. Area values (eV×cps), obtained from spectra having been subjected to background correction (carried out by Shirley method), were subjected to quantitative correction calculation by use of relative sensitivity factors (C=4.079042, F=15.611973) as provided to an analytical software (produced by Jeol System;

SpecXPS Version 1.2.3) as appended to the apparatus, thus calculating the element percentage value of each element. The OH/C ratio was determined by carrying out calculation from these values in accordance with the following calculation equation.

OH/C ratio=[element percentage value of fluorine element]/[element percentage value of carbon element]/3

Referential Example 1

In a reactor as prepared by lidding a jacketed stainless twin-arm kneader of 10 liters in capacity having two sigma-type blades, there was prepared a reaction liquid by dissolving 11.7 g (0.10 mol %) of polyethylene glycol diacrylate (number of ethylene glycol repeating units: 9) into 5,438 g of aqueous solution of sodium acrylate having a neutralization degree of 71.3 mol % (monomer concentration: 39 weight %). Next, dissolved oxygen was removed from this reaction liquid under an atmosphere of nitrogen gas for 30 minutes. Subsequently, 29.34 g of 10 weight % aqueous sodium persulfate solution and 24.45 g of 0.1 weight % aqueous L-ascorbic acid solution were added thereto under stirred conditions. As a result, polymerization started after about 1 minute. Then, the polymerization was carried out in the range of 20 to 95° C. while the forming gel was pulverized. Then, the resultant crosslinked hydrogel polymer (1) having been divided into small pieces having diameters of about 1 to about 3 mm was taken out after 30 minutes from the start of the polymerization. This crosslinked hydrogel polymer (1) was spread onto a metal gauze of 50 meshes (mesh opening size: 300 μm) and then hot-air-dried at 175° C. for 50 minutes, thus obtaining a water-absorbent resin agglomerate comprising a particulate dried material agglomerate which was of an irregular shape and easy to pulverize.

The resultant water-absorbent resin agglomerate was pulverized with a roll mill and then further classified with a JIS standard sieve having a mesh opening size of 600 μm. Next, particles having passed through the 600 μm in the aforementioned operation were classified with a JIS standard sieve having a mesh opening size of 150 μm, whereby water-absorbent resin particles having passed through the JIS standard sieve having the mesh opening size of 150 μm were removed. Then, water-absorbent resin particles remaining on this sieve were taken as water-absorbent resin particles (a). The extractable component content of the water-absorbent resin particles (a) was 7 weight %.

Referential Example 2

A water-absorbent resin agglomerate was obtained in the same way as of Referential Example 1 except that the amount of the polyethylene glycol diacrylate (number of ethylene glycol repeating units: 9) was changed to 6.39 g (0.05 mol %).

The resultant water-absorbent resin agglomerate was pulverized with a roll mill and then further classified with a JIS standard sieve having a mesh opening size of 850 μm. Next, particles having passed through the 850 μm in the aforementioned operation were classified with a JIS standard sieve having a mesh opening size of 150 μm, whereby water-absorbent resin particles having passed through the JIS standard sieve having the mesh opening size of 150 μm were removed. Then, water-absorbent resin particles remaining on this sieve were taken as water-absorbent resin particles (b). The extractable component content of the water-absorbent resin particles (b) was 10.5 weight %.

Example 1

An amount of 500 g of the water-absorbent resin particles (a) having been obtained from the aforementioned Referential Example 1 was uniformly mixed with a surface-treating agent comprising a mixed liquid of 10 g of D-sorbitol and 10 g of pure water, and then the resultant mixture (1) was placed into a mortar mixer (having a stirrer), which was then immersed into an oil bath (as adjusted to 210° C. in temperature) to carry out heat-crosslinking in a stirred state under heat-crosslinking conditions for 20 minutes. Furthermore, the resultant particles were disintegrated to such a degree that they could pass through a JIS standard sieve having a mesh opening size of 600 μm. As a result, a particulate water-absorbent resin composition (1) was obtained. Its physical properties were measured. Their results are shown in Table 1.

Example 2

An amount of 500 g of the water-absorbent resin particles (a) having been obtained from the aforementioned Referential Example 1 was uniformly mixed with a surface-treating agent comprising a mixed liquid of 2.5 g of D-sorbitol, 1.6 g of 1,4-butanediol, and 15 g of pure water, and then the resultant mixture (2) was heat-crosslinked at 210° C. for 20 minutes in the same way as of Example 1. Furthermore, similarly, the resultant particles were disintegrated to such a degree that they could pass through a JIS standard sieve having a mesh opening size of 600 μm. As a result, a particulate water-absorbent resin composition (2) was obtained. Its physical properties were measured. Their results are shown in Table 1.

Example 3

An amount of 500 g of the water-absorbent resin particles (a) having been obtained from the aforementioned Referential Example 1 was uniformly mixed with a surface-treating agent comprising a mixed liquid of 1.25 g of D-sorbitol, 1.6 g of 1,4-butanediol, 1.25 g of 1,2-propanediol, and 15 g of pure water, and then the resultant mixture (3) was heat-crosslinked at 210° C. for 20 minutes in the same way as of Example 1. Furthermore, similarly, the resultant particles were disintegrated to such a degree that they could pass through a JIS standard sieve having a mesh opening size of 600 μm. As a result, a particulate water-absorbent resin composition (3) was obtained. Its physical properties were measured. Their results are shown in Table 1.

Comparative Example 1

An amount of 500 g of the water-absorbent resin particles (a) having been obtained from the aforementioned Referential Example 1 was uniformly mixed with a surface-treating agent comprising a mixed liquid of 1.6 g of 1,4-butanediol, 2.5 g of 1,2-propanediol, and 15 g of pure water, thus obtaining a comparative mixture (1). The resultant comparative mixture (1) was heat-crosslinked at 210° C. for 20 minutes in the same way as of Examples 1 to 3. Furthermore, similarly, the resultant particles were disintegrated to such a degree that they could pass through a JIS standard sieve having a mesh opening size of 600 μm. As a result, a comparative particulate water-absorbent resin composition (1) was obtained. Its physical properties were measured. Their results are shown in Table 1. The comparative particulate water-absorbent resin composition (1) was 322 μm in weight-average particle diameter (D50) and 0.36 in logarithmic standard deviation (σζ) of particle size distribution.

Comparative Example 2

The water-absorbent resin particles (a) having been obtained from the aforementioned Referential Example 1 was, as it was, taken as a comparative particulate water-absorbent resin composition (2). The results of having measured its physical properties are shown in Table 1.

Examples 4 to 9 and Comparative Examples 3 to 9

Particulate water-absorbent resin compositions (4) to (9) and comparative particulate water-absorbent resin compositions (3) to (8) were obtained in the same way as of the aforementioned Example 1 except that the water-absorbent resin particles (having been obtained from the Referential Example), the surface-treating agent, the heat-crosslinking conditions, and the standard sieve used were changed to conditions as shown in Table 2. In addition, commercially available water-absorbent resin particles IM-1000 (produced by Sanyo Chemical Industries, Ltd.) were taken as a comparative particulate water-absorbent resin composition (9). The performances of the resultant particulate water-absorbent resin compositions (4) to (9) and comparative particulate water-absorbent resin compositions (3) to (9) are shown in Tables 2, 3 and 4. In addition, the water content of the particulate water-absorbent resin composition (4) (having been obtained from Example 4) was 0.2 weight %.

TABLE 1

| | | Polyol (B) (weight parts) | D50 (μm) | 850-150 μm particle content (%) | σζ | CRC (g/g) | AAP (g/g) | SFC* | WR (s) | AAP/ WR** | SFC/ WR*** |
|---|---|---|---|---|---|---|---|---|---|---|---|
| Example 1 | Particulate water-absorbent resin composition (1) | 0.98 | 329 | 96.4 | 0.343 | 25.6 | 22.0 | 79 | 83 | 0.27 | 0.951 |
| Example 2 | Particulate water-absorbent resin composition (2) | 0.26 | 323 | 96.4 | 0.345 | 25.9 | 22.3 | 87 | 81 | 0.28 | 1.07 |
| Example 3 | Particulate water-absorbent resin composition (3) | 0.12 | 322 | 96.4 | 0.359 | 26.5 | 23.3 | 85 | 118 | 0.20 | 0.720 |
| Comparative Example 1 | Comparative particulate water-absorbent resin composition (1) | 0.00 | 322 | 96.1 | 0.363 | 26.3 | 23.7 | 88 | 236 | 0.10 | 0.373 |
| Comparative Example 2 | Comparative particulate water-absorbent resin composition (2) | 0.00 | 320 | 96.0 | 0.363 | 32.0 | 8.0 | 3 | 1143 | 0.007 | 0.00262 |

*unit $10^{-7} \times cm^3 \times s \times g^{-1}$
**unit g/g/s
***unit $10^{-7} \times cm^3/g$ As is shown in Table 1 above, the particulate water-absorbent resin composition according to the present invention is greatly excellent in the liquid-sucking-up rate (WR) and also excellent in the balance between the liquid permeability and the liquid-sucking-up property (SFC/WR) or in the balance between the water absorption capacity under load and the liquid-sucking-up property (AAP/WR).

The particulate water-absorbent resin composition according to the present invention is high also in the CRC, AAP, and SFC and further exhibits a fast liquid-sucking-up rate (WR) of not more than 120 seconds. In addition, the particulate water-absorbent resin composition according to the present invention is, in liquid permeation sucking-up efficiency (SFC/WR), not less than 0.15 and thus much higher than conventional ones (around 0.1), and is, in capacity-under-load sucking-up efficiency (AAP/WR), not less than 0.50 and thus much higher than conventional ones (around 0.4).

TABLE 2

| | Water-absorbent resin particles used | Surface-crosslinking agent (numerical values are weight % relative to water-absorbent resin particles used) | Surface-treating conditions Temperature (° C.) | Time (minutes) | Mesh opening size of standard sieve used (μm) |
|---|---|---|---|---|---|
| Example 4 | Particulate water-absorbent resin composition (4) | Water-absorbent resin particles (a) | D-sorbitol: 0.5 1,4-butanediol: 0.3 water: 2.5 | 205 | 25 | 600 |
| Example 5 | Particulate water-absorbent resin composition (5) | Water-absorbent resin particles (a) | D-sorbitol: 0.5 1,4-butanediol: 0.3 water: 2.5 | 200 | 30 | 600 |
| Example 6 | Particulate water-absorbent resin composition (6) | Water-absorbent resin particles (a) | meso-erythritol: 1.2 isopropyl alcohol: 0.5 water: 2.5 | 210 | 40 | 600 |
| Example 7 | Particulate water-absorbent resin composition (7) | Water-absorbent resin particles (a) | D-sorbitol: 0.5 3-ethyl-3-hydroxymethyl-oxetane: 0.1 water: 2.5 | 210 | 50 | 600 |
| Example 8 | Particulate water-absorbent resin composition (8) | Water-absorbent resin particles (b) | D-sorbitol: 0.5 1,4-butanediol: 0.3 water: 2.5 | 210 | 25 | 850 |
| Example 9 | Particulate water-absorbent resin composition (9) | Water-absorbent resin particles (b) | D-sorbitol: 0.5 1,4-butanediol: 0.3 water: 2.5 | 210 | 40 | 850 |
| Comparative Example 3 | Comparative particulate water-absorbent resin composition (3) | Water-absorbent resin particles (a) | 1,2-propylene glycol: 0.5 1,4-butanediol: 0.3 water: 2.5 | 210 | 35 | 600 |
| Comparative Example 4 | Comparative particulate water-absorbent resin composition (4) | Water-absorbent resin particles (a) | 1,2-propylene glycol: 0.5 1,4-butanediol: 0.3 water: 2.5 | 210 | 30 | 600 |
| Comparative Example 5 | Comparative particulate water-absorbent resin composition (5) | Water-absorbent resin particles (a) | glycerol: 1.0 isopropyl alcohol: 0.5 water: 2.5 | 210 | 40 | 600 |
| Comparative Example 6 | Comparative particulate water-absorbent resin composition (6) | Water-absorbent resin particles (b) | polyvinyl alcohol*: 0.12 isopropyl alcohol: 0.5 water: 3.5 | 210 | 45 | 850 |
| Comparative Example 7 | Comparative particulate water-absorbent resin composition (7) | Water-absorbent resin particles (a) | ethylene glycol diglycidyl ether: 0.05 1,2-propylene glycol: 0.5 water: 2.5 | 210 | 30 | 600 |
| Comparative Example 8 | Comparative particulate water-absorbent resin composition (8) | Water-absorbent resin particles (a) | D-sorbitol: 0.5 1,4-butanediol: 0.3 water: 2.5 | 210 | 25 | 300 |

TABLE 2-continued

| | Water-absorbent resin particles used | Surface-crosslinking agent (numerical values are weight % relative to water-absorbent resin particles used) | Surface-treating conditions | | Mesh opening size of standard sieve used (μm) |
|---|---|---|---|---|---|
| | | | Temperature (° C.) | Time (minutes) | |
| Comparative Example 9 | Comparative particulate water-absorbent resin composition (9) | — | — | — | — |

*Polyvinyl alcohol (polymerization degree: 1000, saponification degree: 87)

TABLE 3

| | | D50 (μm) | 850-150 μm particle content (%) | σζ | CRC (g/g) | AAP (g/g) | SFC* | LDV (500-300 μm) (mm/s) |
|---|---|---|---|---|---|---|---|---|
| Example 4 | Particulate water-absorbent resin composition (4) | 337 | 98.3 | 0.300 | 26.8 | 24.5 | 81 | 1.26 |
| Example 5 | Particulate water-absorbent resin composition (5) | 358 | 98.7 | 0.291 | 27.9 | 25.2 | 42 | 0.98 |
| Example 6 | Particulate water-absorbent resin composition (6) | 302 | 96.2 | 0.304 | 24.9 | 20.4 | 39 | 1.61 |
| Example 7 | Particulate water-absorbent resin composition (7) | 297 | 94.8 | 0.320 | 23.6 | 21.4 | 95 | 1.98 |
| Example 8 | Particulate water-absorbent resin composition (8) | 461 | 95.9 | 0.436 | 33.6 | 17.0 | 1.7 | 0.11 |
| Example 9 | Particulate water-absorbent resin composition (9) | 410 | 98.0 | 0.399 | 30.1 | 23.6 | 34 | 0.71 |
| Comparative Example 3 | Comparative particulate water-absorbent resin composition (3) | 328 | 97.9 | 0.321 | 26.5 | 24.9 | 90 | 0.80 |

TABLE 3-continued

| | | D50 (μm) | 850-150 μm particle content (%) | σζ | CRC (g/g) | AAP (g/g) | SFC* | LDV (500-300 μm) (mm/s) |
|---|---|---|---|---|---|---|---|---|
| Comparative Example 4 | Comparative particulate water-absorbent resin composition (4) | 345 | 98.6 | 0.298 | 27.5 | 25.8 | 73 | 0.61 |
| Comparative Example 5 | Comparative particulate water-absorbent resin composition (5) | 358 | 98.7 | 0.291 | 27.9 | 23.8 | 26 | 0.56 |
| Comparative Example 6 | Comparative particulate water-absorbent resin composition (6) | 414 | 97.7 | 0.406 | 30.6 | 9 | 1 | 0.08 |
| Comparative Example 7 | Comparative particulate water-absorbent resin composition (7) | 326 | 94.9 | 0.420 | 25.8 | 23.0 | 43 | 0.94 |
| Comparative Example 8 | Comparative particulate water-absorbent resin composition (8) | 193 | 83.0 | 0.278 | 23.2 | 22.6 | 56 | Immeasurable |
| Comparative Example 9 | Comparative particulate water-absorbent resin composition (9) | 237 | 66.6 | 0.904 | 43.5 | 5 | 0 | 0.05 |

*unit $10^{-7} \times cm^3 \times s \times g^{-1}$

TABLE 4

| | | LDV (Bulk) (mm/s) | Tetra- or more functional polyol content (ppm) | −0.186 × CRC + 5.75 | CRC/WR (g/g/s) | AAP/WR (g/g/s) | SFC/WR*** |
|---|---|---|---|---|---|---|---|
| Example 4 | Particulate water-absorbent resin composition (4) | 1.27 | 3270 | 0.765 | 0.34 | 0.31 | 1.02 |
| Example 5 | Particulate water-absorbent resin composition (5) | 0.99 | 3080 | 0.561 | 0.27 | 0.25 | 0.41 |
| Example 6 | Particulate water-absorbent resin composition (6) | 1.63 | 2540 | 1.119 | 0.40 | 0.33 | 0.63 |

TABLE 4-continued

|  |  | LDV (Bulk) (mm/s) | Tetra- or more functional polyol content (ppm) | −0.186 × CRC + 5.75 | CRC/WR (g/g/s) | AAP/WR (g/g/s) | SFC/WR*** |
| --- | --- | --- | --- | --- | --- | --- | --- |
| Example 7 | Particulate water-absorbent resin composition (7) | 2.00 | 3310 | 1.360 | 0.47 | 0.47 | 0.89 |
| Example 8 | Particulate water-absorbent resin composition (8) | 0.15 | 2690 | −0.500 | 0.04 | 0.02 | 0.00 |
| Example 9 | Particulate water-absorbent resin composition (9) | 0.74 | 0 | 0.151 | 0.21 | 0.17 | 0.24 |
| Comparative Example 3 | Comparative particulate water-absorbent resin composition (3) | 0.80 | 0 | 0.821 | 0.24 | 0.22 | 0.80 |
| Comparative Example 4 | Comparative particulate water-absorbent resin composition (4) | 0.61 | 0 | 0.635 | 0.17 | 0.16 | 0.45 |
| Comparative Example 5 | Comparative particulate water-absorbent resin composition (5) | 0.55 | 0 | 0.561 | 0.18 | 0.15 | 0.17 |
| Comparative Example 6 | Comparative particulate water-absorbent resin composition (6) | 0.08 | 0 | 0.058 | 0.02 | 0.01 | 0.00 |
| Comparative Example 7 | Comparative particulate water-absorbent resin composition (7) | 0.93 | 0 | 0.951 | 0.24 | 0.22 | 0.40 |
| Comparative Example 8 | Comparative particulate water-absorbent resin composition (8) | 0.57 | 2600 | 1.435 | 0.13 | 0.13 | 0.32 |
| Comparative Example 9 | Comparative particulate water-absorbent resin composition (9) | — | 0 | −2.341 | 0.02 | 0.00 | 0.00 |

***unit $10^{-7} \times cm^3/g$

Example 10

An amount of 2.4 weight parts of a mixed solution (having been prepared by mixing 100 weight parts of 50 weight % aqueous solution of aluminum sulfate tetradeca- to octadecahydrates (produced by Kanto Chemical Co., Inc.) and 20 weight parts of 50 weight % aqueous solution of sodium lactate together) was added to 100 weight parts of the particulate water-absorbent resin composition (4) (having been obtained from Example 4) to mix them together under stirring. The resultant water-absorbent resin was uniformly spread on a glass Petri dish, and then this dish was covered with a glass lid and then left in a hot-air drier (as adjusted to 60° C. in temperature) for 60 minutes. Thereafter, the particulate water-absorbent resin composition was taken out and then passed through a mesh opening size of 600 μm with a JIS 600-μm standard sieve, thus obtaining a particulate water-absorbent resin composition (10). The performances of the resultant particulate water-absorbent resin composition (10) are shown in Tables 5 and 6. In addition, the water content of the resultant particulate water-absorbent resin composition (10) was 1.5 weight %.

Example 11

An amount of 2.0 weight parts of 50 weight % aqueous solution of aluminum sulfate tetradeca- to octadecahydrates (produced by Kanto Chemical Co., Inc. was added to 100 weight parts of the particulate water-absorbent resin composition (5) (having been obtained from Example 5) to mix them together under stirring. The resultant water-absorbent resin was uniformly spread on a glass Petri dish, and then this dish was covered with a glass lid and then left in a hot-air drier (as adjusted to 60° C. in temperature) for 60 minutes. Thereafter, the particulate water-absorbent resin composition was taken out and then passed through a mesh opening size of 600 μm with a JIS 600-μm standard sieve, thus obtaining a particulate water-absorbent resin composition (11). The performances of the resultant particulate water-absorbent resin composition (11) are shown in Tables 5 and 6.

Comparative Example 10

A comparative particulate water-absorbent resin composition (10) was obtained by carrying out the same way as of Example 10 except that the particulate water-absorbent resin composition (4) as used for carrying out Example 10 was replaced with the comparative particulate water-absorbent resin composition (3). The performances of the resultant comparative particulate water-absorbent resin composition (10) are shown in Tables 5 and 6.

Comparative Example 11

An amount of 0.1 weight part of REOLOSIL QS-20 (produced by Tokuyama Co., Ltd.) was added to 100 weight parts of the comparative particulate water-absorbent resin composition (3) (having been obtained from Comparative Example 3) to mix them together. After this mixing, the particulate water-absorbent resin composition was passed through a mesh opening size of 600 μm with a JIS 600-μm standard sieve, thus obtaining a comparative particulate water-absorbent resin composition (11). The performances of the resultant comparative particulate water-absorbent resin composition (11) are shown in Tables 5 and 6.

TABLE 5

| | | Particulate water-absorbent resin composition after surface-crosslinking | Treating agent after surface-crosslinking (numerical values are amounts relative to particulate water-absorbent resin composition after surface-crosslinking) | D50 (μm) | 850-150 μm particle content (%) | σζ |
|---|---|---|---|---|---|---|
| Example 10 | Particulate water-absorbent resin composition (10) | Particulate water-absorbent resin composition (4) | 50% aqueous $Al_2(SO_4)_3$ solution: 2 wt % 50% aqueous Na lactate solution: 0.4 wt % | 334 | 98.3 | 0.306 |
| Example 11 | Particulate water-absorbent resin composition (11) | Particulate water-absorbent resin composition (5) | 50% aqueous $Al_2(SO_4)_3$ solution: 2 wt % | 359 | 98.7 | 0.289 |
| Comparative Example 10 | Comparative particulate water-absorbent resin composition (10) | Comparative particulate water-absorbent resin composition (3) | 50% aqueous $Al_2(SO_4)_3$ solution: 2 wt % 50% aqueous Na lactate solution: 0.4 wt % | 322 | 96.9 | 0.339 |
| Comparative Example 11 | Comparative particulate water-absorbent resin composition (11) | Comparative particulate water-absorbent resin composition (3) | REOLOSIL QS-20: 0.1 wt % | 328 | 97.8 | 0.321 |

TABLE 6

| | Particulate water-absorbent resin composition after surface-crosslinking | | CRC (g/g) | AAP (g/g) | SFC* | LDV (500-300 μm) (mm/s) | LDV (Bulk) (mm/s) | −0.186 × CRC + 5.75 |
|---|---|---|---|---|---|---|---|---|
| Example 10 | Particulate water-absorbent resin composition (10) | Particulate water-absorbent resin composition (4) | 26.3 | 23.2 | 137 | 1.79 | 1.77 | 0.858 |
| Example 11 | Particulate water-absorbent resin composition (11) | Particulate water-absorbent resin composition (5) | 27.9 | 23.6 | 99 | 1.56 | 1.52 | 0.561 |
| Comparative Example 10 | Comparative particulate water-absorbent resin composition (10) | Comparative particulate water-absorbent resin composition (3) | 26.4 | 23.7 | 143 | 0.82 | 0.83 | 0.840 |
| Comparative Example 11 | Comparative particulate water-absorbent resin composition (11) | Comparative particulate water-absorbent resin composition (3) | 26.2 | 21.5 | 125 | 0.85 | 1.20 | 0.877 |

*unit $10^{-7} \times cm^3 \times s \times g^{-1}$

Examples 12 and 13 and Comparative Examples 12 and 13

The OH/C ratios of the particulate water-absorbent resin compositions were measured. Shown in Table 7 are: the particulate water-absorbent resin compositions used for the measurement; and the results of the measurement.

TABLE 7

| | Particulate water-absorbent resin composition | OH/C ratio |
|---|---|---|
| Example 12 | Particulate water-absorbent resin composition (4) | 0.097 |
| Example 13 | Particulate water-absorbent resin composition (11) | 0.049 |
| Comparative Example 12 | Comparative particulate water-absorbent resin composition (3) | 0.016 |
| Comparative Example 13 | Comparative particulate water-absorbent resin composition (10) | 0.015 |

Referential Example 3

The particulate water-absorbent resin composition (4) (having been obtained from Example 4) was pulverized by hammering it. The pulverized particulate water-absorbent resin composition was 143 μm in weight-average particle diameter (D50). The OH/C ratio of the pulverized particulate water-absorbent resin composition was measured. As a result, it was 0.012.

Example 14

Preparation for Test of Liquid Injection into Absorbent Structure

An amount of 80 weight parts of the particulate water-absorbent resin composition (4) (having been obtained from Example 4) and 20 weight parts of wood-pulverized pulp were mixed together by a mixer in a dry manner. The resultant mixture was shaped into a web of a size of 440 mm×120 mm. This web was pressed by a pressure of 2 kg/cm² for 5 seconds, thus obtaining an absorbent structure having a basis weight of 280 g/m². Subsequently, a liquid-impermeable polypropylene-made back sheet, the aforementioned absorbent structure, and a liquid-permeable polyethylene-made top sheet were stuck on each other in that order with a double-coated tape, thus obtaining an absorbent article. On this absorbent article, there was put a transparent acrylic resin-made flat plate (500 mm×150 mm) (its central portion was provided with a bottom-through cylinder of 70 mm in diameter and 90 mm in height). Further on this flat plate, there was put a weight so that a load of 0.3 psi would be applied uniformly.

<Liquid Injection Test>:

An amount of 75 ml of 0.9 weight % physiological saline solution (having been adjusted in the range of 35 to 37° C. in temperature) was poured into the cylinder at a stroke, and the time was measured from this injection until the liquid in the cylinder was absorbed by the absorbent structure to thus become unseen with the eye (first time). Then, 5 minutes later than the first-time liquid injection, similarly to the first time, 75 ml of 0.9 weight % physiological saline solution (having been adjusted in the range of 35 to 37° C. in temperature) was poured into the cylinder at a stroke, and the time was measured from this injection until the liquid in the cylinder was absorbed by the absorbent structure to thus become unseen with the eye (second time). Then, 5 minutes later than the second-time liquid injection, similarly to the first time, 75 ml of 0.9 weight % physiological saline solution (having been adjusted in the range of 35 to 37° C. in temperature) was poured into the cylinder at a stroke, and the time was measured from this injection until the liquid in the cylinder was absorbed by the absorbent structure to thus become unseen with the eye (third time). Then, 5 minutes later than the third-time liquid injection, similarly to the first time, 75 ml of 0.9 weight % physiological saline solution (having been adjusted in the range of 35 to 37° C. in temperature) was poured into the cylinder at a stroke, and the time was measured from this injection until the liquid in the cylinder was absorbed by the absorbent structure to thus become unseen with the eye (fourth time).

<Measurement of Wet-Back Amount>:

Ten minutes later than the fourth-time liquid injection, the weight and the acrylic resin-made flat plate were removed. Subsequently, on the absorbent article, there was put a 30-ply paper towel (Kitchen Towel WRG22 (50C) produced by Oji Nepia Paper-Manufacturing Co., Ltd.), and further thereon, there was put the acrylic resin-made flat plate, and then they were left further under a load of 20 g/cm$^2$ for 1 minute. Then, the change in weight of the paper towel was measured, whereby the amount of the liquid having been absorbed by the paper towel was determined as the wet-back amount (g).

The obtained results are shown in Table 8.

Comparative Examples 14 and 15

The tests were carried out in the same way as of Example 14 except that the particulate water-absorbent resin composition (4) (having been obtained from Example 4) was replaced with the comparative particulate water-absorbent resin composition (3) (having been obtained from Comparative Example 3) and the comparative particulate water-absorbent resin composition (5) (having been obtained from Comparative Example 5) respectively.

The obtained results are shown in Table 8.

INDUSTRIAL APPLICATION

The present invention safely and easily provides a particulate water-absorbent resin composition which combines the "liquid permeability" and "liquid-sucking-up property" (which have hitherto been antithetical physical properties). Because such a particulate water-absorbent resin composition has absorption properties having never been before, this composition can be used favorably for absorbent structures (molded absorbent layer) of such as disposable diapers, and greatly enhances the absorption power of such as diapers, and reduces the leakage.

The invention claimed is:

1. A particulate water-absorbent resin composition, which is a particulate water-absorbent resin composition comprising a water-absorbent resin (A) of a crosslinked structure obtained by polymerizing an acid-group-containing unsaturated monomer and surface-crosslinking the resulting resin, which composition has a particle size such that particles in the range of 850 to 150 μm, but not including 850 μm, account for not less than 90 weight % of the entirety, and which composition contains a tetra- or more functional polyol (B) at least on surfaces.

2. A particulate water-absorbent resin composition, which is a particulate water-absorbent resin composition comprising a water-absorbent resin (A) of a crosslinked structure obtained by polymerizing an acid-group-containing unsaturated monomer and surface-crosslinking the resulting resin, which composition contains a tetra- or more functional polyol (B) and a tri- or more functional polycation at least on surfaces.

3. A particulate water-absorbent resin composition according to claim 2, which has a particle size such that particles in the range of 850 to 150 μm, but not including 850 μm, account for not less than 90 weight % of the entirety.

4. A particulate water-absorbent resin composition, which is a particulate water-absorbent resin composition comprising a water-absorbent resin (A) of a crosslinked structure obtained by polymerizing an acid-group-containing unsaturated monomer and surface-crosslinking the resulting resin,

TABLE 8

| | | Liquid injection test | | | | Wet-back |
| --- | --- | --- | --- | --- | --- | --- |
| | | First time (s) | Second time (s) | Third time (s) | Fourth time (s) | amount (g) |
| Example 14 | Particulate water-absorbent resin composition (4) | 22 | 26 | 34 | 48 | 12 |
| Comparative Example 14 | Comparative particulate water-absorbent resin composition (3) | 32 | 32 | 40 | 57 | 17 |
| Comparative Example 15 | Comparative particulate water-absorbent resin composition (5) | 37 | 38 | 55 | 72 | 24 | which composition has a particle size such that particles in the range of 850 to 150 μm, but not including 850 μm, account for not less than 90 weight % of the entirety, and which composition satisfies the following relation:

liquid distribution velocity(LDV)(mm/s)>−0.186× water absorption capacity without load(*CRC*)(g/g)+5.75 wherein LDV>0.10 (mm/s).

5. A particulate water-absorbent resin composition, which is a particulate water-absorbent resin composition comprising a water-absorbent resin (A) of a crosslinked structure obtained by polymerizing an acid-group-containing unsaturated monomer and surface-crosslinking the resulting resin, which composition has a particle size such that particles in the range of 850 to 150 μm, but not including 850 μm, account for not less than 90 weight % of the entirety, and which composition is in the range of 0.03 to 0.15 in surface OH/C ratio as determined by photoelectron spectrometry.

6. A particulate water-absorbent resin composition according to claim 4, which contains a tetra- or more functional polyol (B) at least on surfaces.

7. A particulate water-absorbent resin composition according to claim 1, wherein the water-absorbent resin (A) is in the range of 300 to 600 μm in weight-average particle diameter (D50) and in the range of 0.25 to 0.45 in logarithmic standard deviation (σζ) of particle size distribution.

8. A particulate water-absorbent resin composition according to claim 1, wherein the tetra- or more functional polyol (B) is contained in the range of 0.01 to 20 weight % relative to the water-absorbent resin (A).

9. A particulate water-absorbent resin composition according to claim 1, wherein the tetra- or more functional polyol (B) is a sugar alcohol.

10. A particulate water-absorbent resin composition according to claim 1, which is not less than 20 g/g in water absorption capacity without load (CRC).

11. A particulate water-absorbent resin composition according to claim 1, which is not less than 20 g/g in water absorption capacity under load (AAP).

12. A particulate water-absorbent resin composition according to claim 1, which is not less than 10 (unit: $10^{-7} \times cm^3 \times s \times g^{-1}$) in saline flow conductivity (SFC).

13. A particulate water-absorbent resin composition according to claim 1, which is not less than 0.15 (g/g/s) in water absorption capacity without load (CRC) (g/g)/liquid-sucking-uprate-(WR) (s).

14. A particulate water-absorbent resin composition according to claim 1, which is not less than 0.15 (g/g/s) in water absorption capacity under load (AAP) (g/g)/liquid-sucking-up rate (WR) (s).

15. A particulate water-absorbent resin composition according to claim 1, which is not less than 0.50 (unit: $10^{-7} \times cm^3 \times g^{-1}$) in saline flow conductivity (SFC) (unit: $10^{-7} \times cm^3 \times s \times g^{-1}$)/liquid-sucking-up rate (WR) (s).

16. A particulate water-absorbent resin composition according to claim 1, which is in the range of 300 to 600 μm in weight-average particle diameter (D50) and in the range of 0.25 to 0.45 in logarithmic standard deviation (σζ) of particle size distribution.

17. A process for production of a particulate water-absorbent resin composition, which is a process for production of a particulate water-absorbent resin composition including a water-absorbent resin (A) of a crosslinked structure obtained by polymerizing an acid-group-containing unsaturated monomer and surface-crosslinking the resulting polymerization reaction product, wherein the water-absorbent resin (A) is such that particles in the range of 850 to 150 μm, but not including 850 μm, account for not less than 90 weight % of the entirety, and further wherein the process includes a step of mixing the water-absorbent resin (A) and a tetra- or more functional polyol (B) together.

18. A process according to claim 17 for production of a particulate water-absorbent resin composition, wherein the tetra- or more functional polyol (B) is a sugar alcohol.

19. A process according to claim 17 for production of a particulate water-absorbent resin composition, wherein the water-absorbent resin (A) is in the range of 300 to 600 μm in weight-average particle diameter (D50) and in the range of 0.25 to 0.45 in logarithmic standard deviation(σζ) of particle size distribution.

20. A process according to claim 17 for production of a particulate water-absorbent resin composition, which further includes a step of carrying out a heat treatment so that 10 to 90% of the mixed tetra- or more functional polyol (B) will remain unreacted in the particulate water-absorbent resin composition.

21. A process according to claim 17 for production of a particulate water-absorbent resin composition, wherein the water-absorbent resin (A) is obtained by reacting the polymerization reaction product with a surface-crosslinking agent (C) other than the tetra- or more functional polyol (B).

* * * * *